US008556728B2

(12) United States Patent
Walker et al.

(10) Patent No.: US 8,556,728 B2
(45) Date of Patent: Oct. 15, 2013

(54) METHOD AND APPARATUS FOR OUTPUTTING A RESULT OF A GAME VIA A CONTAINER

(75) Inventors: Jay S. Walker, Ridgefield, CT (US); James A. Jorasch, Stamford, CT (US); John M. Packes, Jr., Hawthorne, NY (US); Robert C. Tedesco, Huntington, CT (US)

(73) Assignee: James A. Jorasch, New York, NY (US)

( * ) Notice: Subject to any disclaimer, the term of this patent is extended or adjusted under 35 U.S.C. 154(b) by 1461 days.

(21) Appl. No.: 11/424,008

(22) Filed: Jun. 14, 2006

(65) Prior Publication Data
US 2006/0234793 A1 Oct. 19, 2006

Related U.S. Application Data

(63) Continuation of application No. 10/835,422, filed on Apr. 29, 2004, now Pat. No. 7,553,234, which is a continuation-in-part of application No. 09/165,089, filed on Oct. 1, 1998, now Pat. No. 6,751,730, which is a continuation-in-part of application No. 08/677,544, filed on Aug. 8, 1996, now Pat. No. 5,970,143, which is a continuation-in-part of application No. 08/561,668, filed on Nov. 22, 1995, now Pat. No. 5,768,382, and a continuation-in-part of application No. 08/628,920, filed on Apr. 8, 1996, now Pat. No. 5,828,751.

(51) Int. Cl.
*G07F 17/32* (2006.01)
(52) U.S. Cl.
USPC .................. 463/43; 463/16; 463/44; 713/161
(58) Field of Classification Search
USPC .............................................. 463/16, 43, 44
See application file for complete search history.

(56) References Cited

U.S. PATENT DOCUMENTS 3,943,336 A 3/1976 Dillard
3,990,558 A 11/1976 Ehrat ............................ 194/4 R
(Continued)

FOREIGN PATENT DOCUMENTS

EP 0 132 782 A2 2/1985
EP 0 154 972 A2 9/1985
(Continued)

OTHER PUBLICATIONS

Kouides et al. "A Performance-based reimbursement for influenza immunization in the elderly", Am J Prev Med., 1993, All, accessed Mar. 10, 2008, http://www.ncbi.nlm.nih.gov/pubmed/8398226.*

(Continued)

*Primary Examiner* — Omkar Deodhar
(74) *Attorney, Agent, or Firm* — Carson C. K. Fincham; Fincham Downs, LLC

(57) ABSTRACT

A method and apparatus is disclosed that documents and authenticates cap removal data. According to a first aspect of the present invention, the apparatus measures a parameter indicative of the number of times that a cap has been removed by a user. The apparatus also encodes at least the parameter indicative of the cap removal data, thereby deriving encoded cap removal data. The apparatus outputs the encoded cap removal data to a user. According to a second aspect of the present invention, another apparatus receives the encoded cap removal data and decodes it to authenticate the cap removal data. According to a third aspect of the present invention, a medicine container is operable to output a result of a game based on cap removal data associated with the medicine container.

28 Claims, 9 Drawing Sheets

(56) References Cited

U.S. PATENT DOCUMENTS

| | | | |
|---|---|---|---|
| 4,047,000 A | 9/1977 | Bryant | |
| 4,108,364 A | 8/1978 | Tanaka | |
| 4,123,747 A | 10/1978 | Lancto | |
| 4,223,801 A | 9/1980 | Carlson | |
| 4,253,158 A | 2/1981 | McFiggans | |
| 4,275,384 A | 6/1981 | Hicks | |
| 4,361,408 A * | 11/1982 | Wirtschafter | 368/10 |
| 4,376,299 A | 3/1983 | Rivest | |
| 4,473,884 A | 9/1984 | Behl | |
| 4,526,474 A | 7/1985 | Simon | 368/10 |
| 4,573,606 A | 3/1986 | Lewis | |
| 4,588,303 A | 5/1986 | Wirtschafter et al. | 368/10 |
| 4,616,316 A | 10/1986 | Hanpeter et al. | 364/413 |
| 4,637,051 A | 1/1987 | Clark | |
| 4,641,346 A | 2/1987 | Clark | |
| 4,641,347 A | 2/1987 | Clark | |
| 4,658,093 A | 4/1987 | Hellman | 380/25 |
| 4,660,221 A | 4/1987 | Dlugos | |
| 4,666,160 A | 5/1987 | Hamilton | |
| 4,682,299 A | 7/1987 | McIntosh et al. | |
| 4,695,954 A | 9/1987 | Rose et al. | 364/413 |
| 4,766,542 A | 8/1988 | Pilarczyk | |
| 4,768,176 A | 8/1988 | Kehr | |
| 4,768,177 A | 8/1988 | Kehr et al. | |
| 4,782,966 A | 11/1988 | Thackrey | 215/230 |
| 4,786,940 A | 11/1988 | Daniele | 355/6 |
| 4,803,625 A | 2/1989 | Fu et al. | 364/413.03 |
| 4,807,287 A | 2/1989 | Tucker | |
| 4,831,438 A | 5/1989 | Bellman, Jr. et al. | 348/148 |
| 4,835,713 A | 5/1989 | Pastor | |
| 4,838,275 A | 6/1989 | Lee | |
| 4,855,580 A | 8/1989 | Van Maanen | |
| 4,856,787 A * | 8/1989 | Itkis | 273/237 |
| 4,899,839 A | 2/1990 | Dessertine et al. | 177/25.19 |
| 4,926,572 A | 5/1990 | Holmes | |
| 4,939,705 A | 7/1990 | Hamilton et al. | |
| 4,971,221 A | 11/1990 | Urquhart et al. | 221/2 |
| 4,972,480 A | 11/1990 | Rosen | |
| 5,001,752 A | 3/1991 | Fischer | 380/23 |
| 5,014,798 A | 5/1991 | Glynn | 177/25.19 |
| 5,016,172 A | 5/1991 | Dessertine | 364/413.02 |
| 5,022,080 A | 6/1991 | Durst et al. | 380/23 |
| 5,027,395 A | 6/1991 | Anderson et al. | 380/4 |
| 5,036,461 A | 7/1991 | Elliott et al. | 364/408 |
| 5,050,212 A | 9/1991 | Dyson | 380/25 |
| 5,073,931 A | 12/1991 | Audebert et al. | 380/23 |
| 5,075,862 A | 12/1991 | Doeberl et al. | |
| 5,083,271 A | 1/1992 | Thacher et al. | 364/411 |
| 5,112,051 A | 5/1992 | Darling et al. | 273/148 B |
| 5,136,646 A | 8/1992 | Haber et al. | 380/49 |
| 5,136,647 A | 8/1992 | Haber et al. | 380/49 |
| 5,142,484 A | 8/1992 | Kaufman et al. | 222/638 |
| 5,153,837 A | 10/1992 | Shaffer | |
| 5,155,680 A | 10/1992 | Wiedemer | 364/406 |
| 5,157,726 A | 10/1992 | Merkle et al. | 380/23 |
| 5,189,700 A | 2/1993 | Blandford | 380/23 |
| 5,193,114 A | 3/1993 | Moseley | 380/23 |
| 5,200,891 A | 4/1993 | Kehr | |
| 5,202,923 A | 4/1993 | Kuriyama | 380/50 |
| 5,206,899 A * | 4/1993 | Gupta et al. | 379/120 |
| 5,210,785 A | 5/1993 | Sato | |
| 5,243,652 A | 9/1993 | Teare et al. | |
| 5,243,654 A | 9/1993 | Hunter | 380/51 |
| 5,259,029 A | 11/1993 | Duncan, Jr. | 380/4 |
| 5,288,978 A | 2/1994 | Iijima | 235/380 |
| 5,297,205 A | 3/1994 | Audebert | |
| 5,298,883 A | 3/1994 | Pilney | |
| 5,299,701 A | 4/1994 | Barker | |
| 5,319,710 A | 6/1994 | Atalla et al. | 380/23 |
| 5,333,106 A | 7/1994 | Lanpher et al. | |
| 5,347,579 A | 9/1994 | Blandford | 380/25 |
| 5,347,580 A | 9/1994 | Molva et al. | 380/25 |
| 5,349,642 A | 9/1994 | Kingdon | 380/25 |
| 5,351,293 A | 9/1994 | Michener et al. | 380/21 |
| 5,355,413 A | 10/1994 | Ohno | 380/24 |
| 5,359,510 A | 10/1994 | Sabaliauskas | 364/410 |
| 5,367,573 A | 11/1994 | Quimby | |
| 5,372,276 A | 12/1994 | Daneshvar | 221/2 |
| 5,377,268 A | 12/1994 | Hunter | 380/23 |
| 5,386,468 A | 1/1995 | Akiyama et al. | 380/25 |
| 5,392,952 A | 2/1995 | Bowden | |
| 5,393,057 A | 2/1995 | Marnell | |
| 5,400,319 A | 3/1995 | Fite et al. | 369/275.5 |
| RE34,954 E | 5/1995 | Haber et al. | 380/49 |
| 5,412,575 A | 5/1995 | Constant et al. | 364/464.01 |
| 5,414,841 A | 5/1995 | Bingham | |
| 5,416,840 A | 5/1995 | Cane | |
| 5,434,918 A | 7/1995 | Kung et al. | 380/25 |
| 5,448,641 A | 9/1995 | Pintsov et al. | |
| 5,463,547 A | 10/1995 | Markowitz | |
| 5,464,971 A | 11/1995 | Sutcliffe | |
| 5,472,113 A | 12/1995 | Shaw | 221/7 |
| 5,490,217 A | 2/1996 | Wang | |
| 5,497,419 A | 3/1996 | Hill | 380/9 |
| 5,499,249 A | 3/1996 | Agrawal | |
| 5,499,294 A | 3/1996 | Friedman | 380/10 |
| 5,500,897 A | 3/1996 | Hartman, Jr. | |
| 5,508,731 A | 4/1996 | Kohorn | 348/1 |
| 5,539,822 A | 7/1996 | Lett | 380/20 |
| 5,549,117 A | 8/1996 | Tacklind | |
| 5,564,429 A | 10/1996 | Bornn | |
| 5,569,082 A * | 10/1996 | Kaye | 463/17 |
| 5,583,831 A | 12/1996 | Churchill et al. | 368/10 |
| 5,589,838 A | 12/1996 | McEwan | |
| 5,600,706 A | 2/1997 | Dunn | |
| 5,623,242 A | 4/1997 | Dawson, Jr. | |
| 5,626,144 A | 5/1997 | Tacklind | |
| 5,638,186 A | 6/1997 | Motoyama | |
| 5,641,091 A | 6/1997 | Daneshvar | 221/3 |
| 5,642,731 A | 7/1997 | Kehr | |
| 5,646,912 A | 7/1997 | Cousin | 368/10 |
| 5,646,994 A | 7/1997 | Hill | 380/9 |
| 5,657,236 A | 8/1997 | Conkright | |
| 5,678,182 A | 10/1997 | Miller | |
| 5,678,571 A | 10/1997 | Brown | 128/898 |
| 5,695,091 A | 12/1997 | Winings | |
| 5,704,366 A | 1/1998 | Tacklind | |
| 5,710,551 A | 1/1998 | Ridgeway | 340/870.09 |
| 5,722,418 A | 3/1998 | Bro | |
| 5,752,235 A | 5/1998 | Kehr | |
| 5,757,271 A | 5/1998 | Andrews | |
| 5,758,288 A | 5/1998 | Dunn | |
| 5,761,309 A | 6/1998 | Ohashi | |
| 5,768,382 A | 6/1998 | Schneier et al. | 380/23 |
| 5,774,865 A | 6/1998 | Glynn | 705/2 |
| 5,779,549 A | 7/1998 | Walker et al. | 463/42 |
| 5,794,207 A | 8/1998 | Walker et al. | 705/1 |
| 5,800,264 A | 9/1998 | Pascal et al. | 463/16 |
| 5,828,751 A | 10/1998 | Walker et al. | 380/25 |
| 5,831,859 A | 11/1998 | Medeiros | |
| 5,850,344 A | 12/1998 | Conkright | 364/479.01 |
| 5,850,447 A | 12/1998 | Peyret | 380/25 |
| 5,852,408 A | 12/1998 | Christiansen | |
| 5,852,590 A | 12/1998 | De la Huerga | |
| H1782 H | 2/1999 | Wicks | |
| 5,867,821 A | 2/1999 | Ballantyne et al. | 705/2 |
| 5,871,398 A | 2/1999 | Schneier et al. | 463/16 |
| 5,899,998 A | 5/1999 | McGauley | |
| 5,911,132 A | 6/1999 | Sloane | |
| 5,913,197 A | 6/1999 | Kameda | |
| 5,923,018 A | 7/1999 | Kameda | |
| 5,923,763 A | 7/1999 | Walker et al. | |
| 5,950,630 A | 9/1999 | Portwood | |
| 5,950,632 A | 9/1999 | Reber et al. | |
| 5,954,641 A | 9/1999 | Kehr et al. | |
| 5,960,403 A * | 9/1999 | Brown | 705/2 |
| 5,963,136 A | 10/1999 | O'Brien | |
| 5,969,678 A | 10/1999 | Stewart | |
| 5,970,143 A | 10/1999 | Schneier et al. | 380/23 |
| 6,002,427 A | 12/1999 | Kipust | |
| 6,004,020 A | 12/1999 | Bartur | |
| 6,014,432 A | 1/2000 | Modney | |
| 6,018,289 A | 1/2000 | Sekura | |
| 6,022,315 A | 2/2000 | Iliff | |

(56) References Cited

U.S. PATENT DOCUMENTS

| | | | |
|---|---|---|---|
| 6,032,085 A | 2/2000 | Laurent | |
| 6,070,761 A | 6/2000 | Bloom | |
| 6,108,685 A | 8/2000 | Kutzik et al. | |
| 6,151,586 A | 11/2000 | Brown | |
| 6,167,362 A | 12/2000 | Brown et al. | 703/11 |
| 6,182,219 B1 | 1/2001 | Feldbau | |
| 6,188,766 B1 | 2/2001 | Kocher | |
| 6,198,685 B1 | 3/2001 | Sudo | |
| 6,259,654 B1 | 7/2001 | de la Huerga | |
| 6,294,999 B1 | 9/2001 | Yarin | |
| 6,335,907 B1 | 1/2002 | Momich et al. | 368/10 |
| 6,375,038 B1 | 4/2002 | Daansen | |
| 6,484,027 B1 | 11/2002 | Mauney et al. | |
| 6,529,446 B1 | 3/2003 | de la Huerga | |
| 6,689,103 B1 | 2/2004 | Palasis | |
| 6,771,174 B2 | 8/2004 | Broas | 340/573.1 |
| 7,170,409 B2 | 1/2007 | Ehrensvard et al. | 340/539.26 |
| 7,170,823 B2 | 1/2007 | Fabricius et al. | 368/10 |
| 2003/0060286 A1 | 3/2003 | Walker et al. | 463/42 |
| 2008/0077430 A1 | 3/2008 | Singer | 705/2 |

FOREIGN PATENT DOCUMENTS

| | | |
|---|---|---|
| EP | 0 331 352 A2 | 9/1989 |
| EP | 440021 | 8/1991 |
| EP | 0 526 166 A2 | 2/1993 |
| EP | 0 526 166 A3 | 2/1993 |
| EP | 0547837 B1 | 6/1993 |
| EP | 0684575 | 12/1994 |
| EP | 0727894 A1 | 8/1996 |
| GB | 2 065 030 A | 6/1981 |
| GB | 2240543 A | 8/1991 |
| JP | 03029661 A | 2/1991 |
| JP | 403256876 A | 11/1991 |
| JP | 7/68051 | 3/1995 |
| JP | 7/255950 | 10/1995 |
| WO | WO 95/09386 | 4/1995 |
| WO | WO 95/26009 | 9/1995 |
| WO | WO 00/19962 A2 | 4/2000 |
| WO | PCT/US2005/014829 | 12/2007 |

OTHER PUBLICATIONS

Coca-Cola, American Express uncork Hawaii vacations contest, http://www.highbeam.com/doc/1G1-7615573.html, Magenheim, Henry, Travel Weekly, May 25, 1989.*
Simmons, Gustavus J., "Proceedings of the 1983 Symposium on Security and Privacy", Sponsored by the Technical Committee on Security and Privacy, IEEE Computer Society, Apr. 25-27, 1983, pp. 61-66, 7 pp.
Morris, Daniel C., "The ten basics of system security", Computers in Healthcare, Nov. 1989, Section: vol. 10, No. 11, p. 41, ISSN: 0745-1075, 3 pp.
Gardner, Elizabeth, "Computer dilemma: clinical access vs. confidentiality", Modern Healthcare, Nov. 3, 1989, pp. 32-34, 38, 40, 42, 6 pp.
"Monitors compliance; Medi-Monitor programmable medication dispenser; Rx: Mass Market Retail Pharmacy", Chain Drug Review, Jul. 30, 1990, Section: vol. 12, No. 21, p. RX8, ISSN: 0164-9914, 2 pp.
Brown, Lowell C. et al., "Computerized Patient Records—CPR and the Law: Plan Now", Health Systems Review, Nov./Dec. 1992, vol. 25, Issue 6, ISSN: 1055-7466, 6 pp.
Heikens, Norm, "Inventor hopes $2^{nd}$ marketing try on medication monitor is charm", Indianapolis Business Journal, Feb. 1, 1993, Section: vol. 13, No. 45, Sec. 1, p. 11A, 3 pp.
Ognibene, Peter, "'Smart Cards Could Save Lives-and Dollars Health care: A computerized personal medical record would assist doctors and pharmacists and avert dangerous errors.", The Los Angeles Times, Apr. 12, 1993, 2 pp.
Amos, Paul J. et al., "Drug cards manage rising prescription costs", Personal Journal, May 1993, vol. 72, Issue 5, ISSN: 0031-5745, 6 pp.
Betts, Mitch, "Smart cards lose out in health reform", Computerworld, Feb. 28, 1994, vol. 28, Issue 9, ISSN: 0010-4841, 2 pp.
Stevens, Larry, "Taking Your Medicine; Doctors Consider Monitors for Patients Who Can't Keep Track of Prescriptions", St. Louis Post-Dispatch, Aug. 22, 1994, Section: Everyday Magazine, p. 1E, 3 pp.
"High-Tech Reminders", St. Louis Post-Dispatch, Aug. 22, 1994, Section: Everyday Magazine, p. 1E, 2 pp.
"Patient financial incentives for compliance, feedback suggested by Medco exec; expanded use of questionnaires in disease management programs planned", FDC Reports: The Pink Sheet Sep. 19, 1994, vol. 56, Issue 38, 4 pp.
Hussar, Daniel A., "Patient compliance: the ongoing challenge facing pharmacy.", American Druggist, Nov. 1994, Section: vol. 211, No. 1, p. 83, ISSN: 0190-5279, 13 pp.
Gannon, Kathi, "Keeping track; new in-home system helps patient stay compliant.", Drug Topics, Feb. 6, 1995, Section: vol. 139, No. 3, p. 60, ISSN: 0012-6616, 2 pp.
"Compliance is a phone call away", Med Ad News, Mar. 1995, Section: p. 12, ISSN: 0745-0907, 2 pp.
Tashkin, Donald, "Multiple dose regimens: impact on compliance bronchiodilator therapy for chronic obstructive pulmonary disease; supplement", Chest, May 1995, Section: vol. 107, No. 5, p. 176S, ISSN: 0012-3692, 9 pp.
Young, David, "Fear Not, Free Enterprise; U.S. Ingenuity Alive and Well", Chicago Tribune, Jun. 26, 1995, Section: Business, p. 3, Zone C, Biz Tips, 1 pg.
Press Release: "First Fully Authenticated Digital Video Surveillance System Features Advanced RSA Security Technology", RSA Data Security, Inc., Oct. 23, 1995, 2 pp.
Schneier, Bruce, "Applied Cryptography, Second Edition—Protocols, Algorithms, and Source Code in C", John Wiley & Sons, Inc., Copyright 1996, Chapter 2, pp. 21, 46, 27 pp.
Resnik, W.M., "Technology Track—Digital Image Authentication", Aquila Technologies Group, Inc., Jan. 17, 1996, 7 pp.
"Conference Coverage (IUATLD) Simplified Medication Monitor Presented", Tuberculosis & Airborne Disease Weekly, Mar. 17, 1997, 2 pp.
"New Line of Telemedical 'Personal Medical Assistants' Will Monitor Patients' Condition and Help Millions Take Prescriptions on Time, In Sequence, and in Proper Dosage", PR Newswire, Apr. 9, 1997, Section: Financial News, 12 pp.
Berg, Jill et al., "An evaluation of a self-management program for adults with asthma", Clinical Nursing Research, Aug. 1997, Section: No. 3, vol. 6, p. 225, ISSN: 1054-7738, 4 pp.
Corden, Zoe M. et al., "Home nebulized therapy for patients with COPD: patient compliance with treatment and its relation to quality of life; chronic obstructive pulmonary disease", Chest, Nov. 1997, Section: No. 5, vol. 112, p. 1278, ISSN: 0012-3692, 6 pp.
"Electronic monitoring gains more acceptance: formerly clunky devices now cheap, user-friendly; devices to track medication compliance", AIDS Alert, Feb. 1998, Section: No. 2, vol. 13, p. 21, ISSN: 0887-0292, 13 pp.
Fried, Lisa I., "Annual Report Part 1: Full Integration Within American Stores", Drug Store News, Apr. 27, 1998, p. 145, 6 pp.
Trueland, Jennifer, "New Drug Hope for Asthma Sufferers", The Scotsman, Jul. 21, 1998, p. 5, 2 pp.
Website: "APREX Clinic-based Patient Compliance/Adherherence", Sep. 14, 1998, 2 pp.
Website: "Exact CM Compliance Monitoring System for Clinical Trials", Exact CM, Sep. 14, 1998, 3 pp.
Pendrak, Robert F., "Information technologies need to protect patient confidentiality.", Healthcare Financial Management, Oct. 1998, Section: No. 10, vol. 52, p. 66, ISSN: 0735-0732, 4 pp.
PCT International Search Report for International Application No. PCT/US 99/21895, now abandoned, in the name of Walker et al., mailed Apr. 19, 2000, 8 pp.
European Patent Office (EPO) Office Action (Communication Pursuant to Article 94(3) EPC), EP Application No. 05 858 343.6, 8 pgs, mailed Jun. 24, 2010.
Schneier, Applied Cryptography 2e, Chapter 2.

(56) References Cited

OTHER PUBLICATIONS

Giuffrida, Antonio et al. "Should we Pay the Patient? Review of Financial Incentives to Enhance Patient Compliance", Sep. 20, 1997, British Medical Journal, 15 pp.
Rubenstein, Ed. "Operators Squelching Shrinkage with Cutting-Edge Liquor-Management Systems", Oct. 6, 1997, Nation's Restaurant News, 4 pp.
"Mid-Atlantic Tests Monitoring Device for CHF Patients", Oct. 1, 1998, Telehealth Magazine, 2 pp.
"Turning on to Radio", Jan. 14, 1999, Packaging Magazine, 4 pp.
"Virtual Nags: New Devices Track Medication Compliance", Mar. 25, 1999, Medical Outcomes and Guidelines Alert, 2 pp.
Elder, Nina. "A Dose in Time; There are Many Ways to Remember to Take Prescription Medicine; Brief", Jul. 1, 1999, Better Homes and Gardens, 2 pp.
Chin, L. Tyler. "Identifying New Uses for Bar Coding Technology." Aug. 1999. Health Data Management, 6 pp.
"Clever Containers." Sep. 6, 1999. Electronics Times, 3 pp.
Moore, Bert. "How to Identify the Odd Item: From Pistons to Casino Chips, Unique Articles are Getting Tagged with Unique Ideas; Technology Information." Nov. 1, 1999. Automatic I.D. News, 13 pp.
Kaiser, Rob. "New Labels May Replace Bar Codes." Nov. 28, 1999. Las Vegas Review-Journal, 3 pp.
Forger, Gary. "Taking Advantage of RF Technologies for Real-Time Control." Nov. 30, 1999. Modern Materials Handling, 5 pp.
"Catalyst Awarded PE Biosystems' Warehouse Management System Project", PR Newswire (to Business and Technology Editors): Dec. 23, 1999, 2 pp.
"We're Different Because We Are Determined to Make Healthcare Better for You." 1999, Oxford Health Plans, 8 pp.
"Exercise Facility Benefit." Dec. 1996, 3 pp.
Weeks, John. "Charting the Mainstream: Doctor-Patient Communication, Women in Medicine, Pharmaceutical Positioning Under Managed Care, and More . . ." Jan. 1995, 6 pp.
Scott, Miriam Basch. "Disease Management, Touted as the Next Frontier, Aims for Quality Care and Reduced Costs", Dec., 1995, Employee Benefit Plan Review, 7 pp.
"Cap for TB, A Clinic-Based Adherence/Compliance Program for Monitoring TB Patients" Sep. 14, 1998, 2 pp.
"Quick Read Reveals Compliance Statistics from Each Dispenser", Sep. 14, 1998, 1 pg.
Holcomb, Henry J. "Keeping Tags on Everything: A New Generation of Smart Tags will Allow Merchants to Better Combat Theft and Fraud, and Make Inventory a Breeze . . .", Aug. 3, 1999, National Post, 5 pp.
Trunk, Christopher. "On the Fast Track to Smart Tags . . .", Sep. 1, 1999, Material Handling Engineering, 6 pp.
"The Product" Jan. 26, 2000, 2 pp.
"Electronic ID, Destron Fearing Electronic Identification Microchip", Feb. 2, 2000, 8 pp.
"The Official Bluetooth Website." http://www bluetoothguide com, Feb. 2, 2000, 2 pp.
Freudenheim, Milt, "Corrective Medicine, New Technology Helps Health Care Avoid Mistakes", Feb. 3, 2000, New York Times, 6 pp.
Dalzell, Michael D. "Pharmacy Copayments: A Double-Edged Sword" Feb. 15, 2000, Managed Care Magazine, 9 pp.
"Kumetrix Technology Overview Painless Blood-Gulcose Monitoring", May 18, 2000, Kumetrix.com, 2 pp.
Toon, John. "Taking the Ouch Out of Needles: Arrays of Micron-Scale Microneedles Offer New Technique for Drug Delivery", Jun. 5, 2000, 4 pp.
"Catalyst Awarded PE Biosystems' Warehouse Management System Project", Dec. 23, 1999, PR Newswire, 3 pp.
"Quick Read' reveals compliance statistics from each dispenser" Dispensing Times by Position [online] [retrieved on Sep. 14,1998], 1pg.
Decision on Appeal for U.S. Appl. No. 09/609,017, mailed Dec. 6, 2006, 11 pp.
Examiner's Answer to Appeal Brief for U.S. Appl. No. 09/609,017 dated Sep. 22, 2004, 51 pp.
Notice of Allowability for U.S. Appl. No. 08/628,920, mailed Feb. 20, 1998, 4 pp.
Notice of Allowance for U.S. Appl. No. 09/609,017 dated Oct. 15, 2007, 7 pp.
Notice of Allowance, U.S. Appl. No. 09/609,017, mailed Mar. 21, 2007, 7 pp.
Office Action for U.S. Appl. No. 08/561,668, mailed Jun. 6, 1997, 6 pp.
Office Action for U.S. Appl. No. 08/628,920, mailed Dec. 22, 1997, 5 pp.
Office Action for U.S. Appl. No. 08/628,920, mailed Jul. 23, 1997, 4 pp.
Office Action for U.S. Appl. No. 08/677,544, mailed Apr. 29, 1998, 4 pp.
Office Action for U.S. Appl. No. 09/165,089, mailed Feb. 7, 2003, 10 pp.
Office Action for U.S. Appl. No. 09/165,089, mailed May 8, 2002, 9 pp.
Office Action for U.S. Appl. No. 09/165,089, mailed Mar. 14, 2001, 11 pp.
Office Action for U.S. Appl. No. 09/165,089, mailed Jul. 17, 2000, 9 pp.
Office Action for U.S. Appl. No. 09/609,017, mailed Aug. 12, 2003, 13 pp.
Office Action for U.S. Appl. No. 09/609,017, mailed Dec. 4, 2002, 12 pp.
Office Action for U.S. Appl. No. 09/609,253 dated Jan. 30, 2008, 18 pp.
Notice of Panel Decision from Pre-Appeal Brief Review U.S. Appl. No. 09/609,253 dated May 22, 2006, 2 pp.
Office Action for U.S. Appl. No. 09/609,253, dated Jul. 26, 2007, 10 pp.
Office Action for U.S. Appl. No. 09/609,253, mailed Jan. 17, 2007, 18 pp.
Office Action for U.S. Appl. No. 09/609,253, mailed Jan. 18, 2006, 9 pp.
Office Action for U.S. Appl. No. 09/609,253, mailed Dec. 30, 2004, 17 pp.
Office Action for U.S. Appl. No. 09/609,253, mailed Mar. 24, 2003, 6 pp.
Office Action for U.S. Appl. No. 09/609,253, mailed Apr. 7, 2004, 27 pp.
Office Action for U.S. Appl. No. 09/609,253, mailed Jul. 17, 2003, 27 pp.
Office Action for U.S. Appl. No. 11/423,881, dated Jan. 9, 2008, 16 pp.
Office Action for U.S. Appl. No. 11/423,881, dated Oct. 20, 2008, 11 pp.
Office Action for U.S. Appl. No. 09/149,025, dated Jul. 7, 1999, 5 pp.
Office Action for U.S. Appl. No. 09/149,025, dated Feb. 1, 2000, 5 pp.
Notice of Allowability for U.S. Appl. No. 09/706,646, dated Mar. 13, 2001, 5 pp.
Office Action for U.S. Appl. No. 11/423,881, dated Jan. 12, 2010, 10 pp.
Office Action for U.S. Appl. No. 11/423,901, dated Mar. 8, 2010, 6 pp.
Jacobson, Terry A., "The Forgotten Cardiac Risk Factor: Noncompliance With Lipid-Lowering Therapy", Medscape Cardiology, Copyright 2004, Hyperlipidemia Expert Column; 10 pp.
Benner, Joshua S. et al., "Association between short-term effectiveness of Statins and long-term adherence to lipid-lowering therapy", Am J Health- Syst Pharm, Jul. 15, 2005, vol. 62, Reports, 8 pp. 1468-1475.
Notice of Allowance for U.S. Appl. No. 11/424,002, mailed Feb. 23, 2009, 6 pp.
Office Action for U.S. Appl. No. 11/424,002, dated Aug. 22, 2008, 6 pp.
Office Action for U.S. Appl. No. 11/424,002, mailed Mar. 18, 2008, 12 pp.
Notice of Allowance for U.S. Appl. No. 10/835,422, dated Mar. 11, 2009, 6 pp.
Office Action for U.S. Appl. No. 10/835,422, dated Sep. 15, 2008, 10 pp.

(56) References Cited

OTHER PUBLICATIONS

Office Action for U.S. Appl. No. 10/835,422, mailed Mar. 18, 2008, 13 pp.
Office Action for U.S. Appl. No. 11/423,997, dated Mar. 18, 2008, 13 pp.
Office Action for U.S. Appl. No. 11/423,997, dated Aug. 18, 2008, 9 pp.
Notice of Allowance for U.S. Appl. No. 11/423,997, dated Aug. 28, 2009, 7 pp.
Office Action for U.S. Appl. No. 11/424,082, dated Sep. 30, 2009, 6 pp.

* cited by examiner

| USER IDENTIFIER 610 | USER NAME 620 | ADDRESS 630 | TELEPHONE NUMBER 635 | POLICY IDENTIFIER 640 | ACCOUNT IDENTIFIER 650 | TAMPERING INDICATION 660 |
|---|---|---|---|---|---|---|
| 123456 | SUE MARVIN | 1 MAIN ST. ANYTOWN, USA | (123) 456-7890 | POL0001 | 5411-0123-9876-0010 | NO |
| 456123 | JOHN SMITH | 22 RIVER PL. METROPOLIS, USA | (345) 123-4567 | POL0002 | 6011-2468-9090-1048 | NO |
| 789654 | GARY JONES | 33 STATE ST. CAPITOL CITY, USA | (111) 444-5555 | POL0003 | 9311-7764-7359-9021 | NO |
| 678543 | AMY ANDREWS | 444 MADISON AVE. SUBURB, USA | (444) 555-6667 | POL0004 | 4040-5858-7325-4901 | YES |

METHOD AND APPARATUS FOR OUTPUTTING A RESULT OF A GAME VIA A CONTAINER

CROSS-REFERENCE TO RELATED CORRESPONDING APPLICATIONS

The present application is a continuation of U.S. patent application Ser. No. 10/835,422, filed Apr. 29, 2004 now U.S. Pat. No. 7,553,234, entitled "METHOD AND APPARATUS FOR OUTPUTTING A RESULT OF A GAME VIA A CONTAINER"; which is a continuation-in-part of commonly owned, U.S. patent application Ser. No. 09/165,089 entitled "METHOD AND APPARATUS FOR DOCUMENTING CAP REMOVAL DATA" filed Oct. 1, 1998, now U.S. Pat. No. 6,751,730 which is a continuation-in-part of U.S. patent application Ser. No. 08/677,544 entitled "REMOTE AUDITING OF COMPUTER GENERATED OUTCOMES AND AUTHENTICATED BILLING AND ACCESS CONTROL SYSTEM USING CRYPTOGRAPHIC AND OTHER PROTOCOLS" filed Aug. 8, 1996 now U.S. Pat. No. 5,970,143, which is a continuation-in-part of U.S. patent application Ser. No. 08/561,668 of the same title filed Nov. 22, 1995, now U.S. Pat. No. 5,768,382; and is further a continuation-in-part of commonly owned, U.S. application Ser. No. 08/628,920 entitled "METHOD AND SYSTEM FOR SECURE MEASUREMENT CERTIFICATION" filed Apr. 8, 1996, now U.S. Pat. No. 5,828,751 the entirety of each of these applications being hereby incorporated by reference herein.

BACKGROUND OF THE INVENTION

A major problem facing the health care industry today is the difficulty of enforcing patient compliance with prescription medications. All too often, patients ignore the directions associated with their prescriptions, consuming more or fewer pills than that recommended by their doctor. Many patients simply forget to take the medication for one or more days, resulting in a lengthened healing process. In some cases, not taking pills according to a precise schedule can result in complications requiring expensive hospital stays or increased time consulting with a physician. These cost increases from the patient's lack of compliance are passed on to health care providers and insurers.

One approach to solving the problem of patient compliance has been the development of modified pill containers which automatically dispense the correct number of pills. U.S. Pat. No. 5,641,091 to Daneshvar is a medication dispensing device which allows a patient to receive his medication on a regular basis. A series of small spaces are arranged in one or more electrically powered rotating trays to allow a proper dose via a window. While this approach makes it easier for a conscientious patient to follow his prescription, forgetful patients may simply let pills "build up" rather than consuming them. Additionally, such devices contain many moving parts that are subject to malfunction and wear. Malfunctions could result in legal liability if the patient was provided access to fewer pills than required by his prescription.

A similar dispensing device is described in U.S. Pat. No. 5,472,113 to Shaw. The automatic pill dispensing device of Shaw has cartridges rotated via an electric motor, electromagnetic clutches, a rotatable shaft, and gears. As with the Daneshvar device, there is no way for a remote third party to know whether or not the device is operating properly and whether the patient is in fact complying with his prescription.

Because third parties such as hospitals and insurance companies would like to have access to patient prescription compliance data, other devices have been created to store data such as how often a pill container has been opened or the time and date that it was opened. U.S. Pat. No. 5,016,172 to Dessertine and U.S. Pat. No. 4,939,705 to Hamilton et al. both describe such an apparatus. These devices, however, either require the user to physically deliver the apparatus to the interested third party for data retrieval and verification, or require that the device have a modem for online connection to the third party. Physical delivery is time consuming and potentially costly for the user, while an online connection requires expensive hardware and greater sophistication on the part of the user.

A need therefore exists for a method and apparatus that addresses the deficiencies of the prior art. Specifically, a need exists for a reliable and efficient method and apparatus for securely measuring, reporting and tracking pill container access data generated in an off-line environment. Accordingly, the shortcomings associated with the related art have heretofore not been adequately addressed. The present invention addresses the deficiencies of the prior art by providing an apparatus and processing approach that have not previously been proposed.

BRIEF DESCRIPTION OF THE DRAWINGS

An understanding of the invention and many of the attendant advantages thereof may be readily obtained by reference to the following detailed description when considered with the accompanying drawings, wherein:

FIG. 6 depicts an exemplary user table stored in the memory of the central controller of FIG. 3;

DETAILED DESCRIPTION

The present invention relates generally to medicine containers. More particularly, the present invention relates to a method and apparatus for documenting and authenticating medicine container cap removal data.

One object of the present invention is to enable a user to document the number of times that he has accessed a pill container by removing the cap, with the cap removal data secured so that a third party can authenticate that the user performed the documented number of cap removals.

An advantage of the present invention is that it enables a user to automatically produce reliably documented cap removal data. Another advantage of the present invention is that it enables a third party to rely on a measurement of the cap removal data by a user of pill containers. Yet another advantage of the present invention is that it enables a third party to provide rebates, discounts, higher reimbursement levels or rewards to a user based on a measurement of the number of cap removals performed by the user.

According to the present invention, a method and apparatus are disclosed for documenting cap removal data. The method includes the step of measuring a number of removals to determine cap removal data. The method further includes the step of encoding the determined cap removal data to derive encoded cap removal data. The method also includes the step of outputting the encoded cap removal data.

The above objects, features and advantages as well as other objects, features and advantages are readily apparent from the detailed description when taken in connection with the accompanying drawings.

Apparatus Architecture

Figure 1:
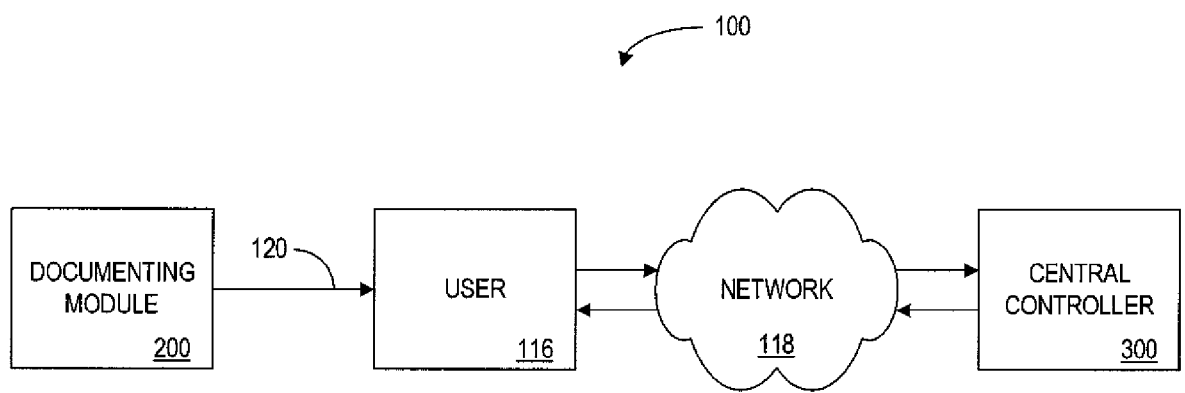
FIG. 1 is a schematic block diagram illustrating the components of a system employing one embodiment of the present invention.
Figure 2:
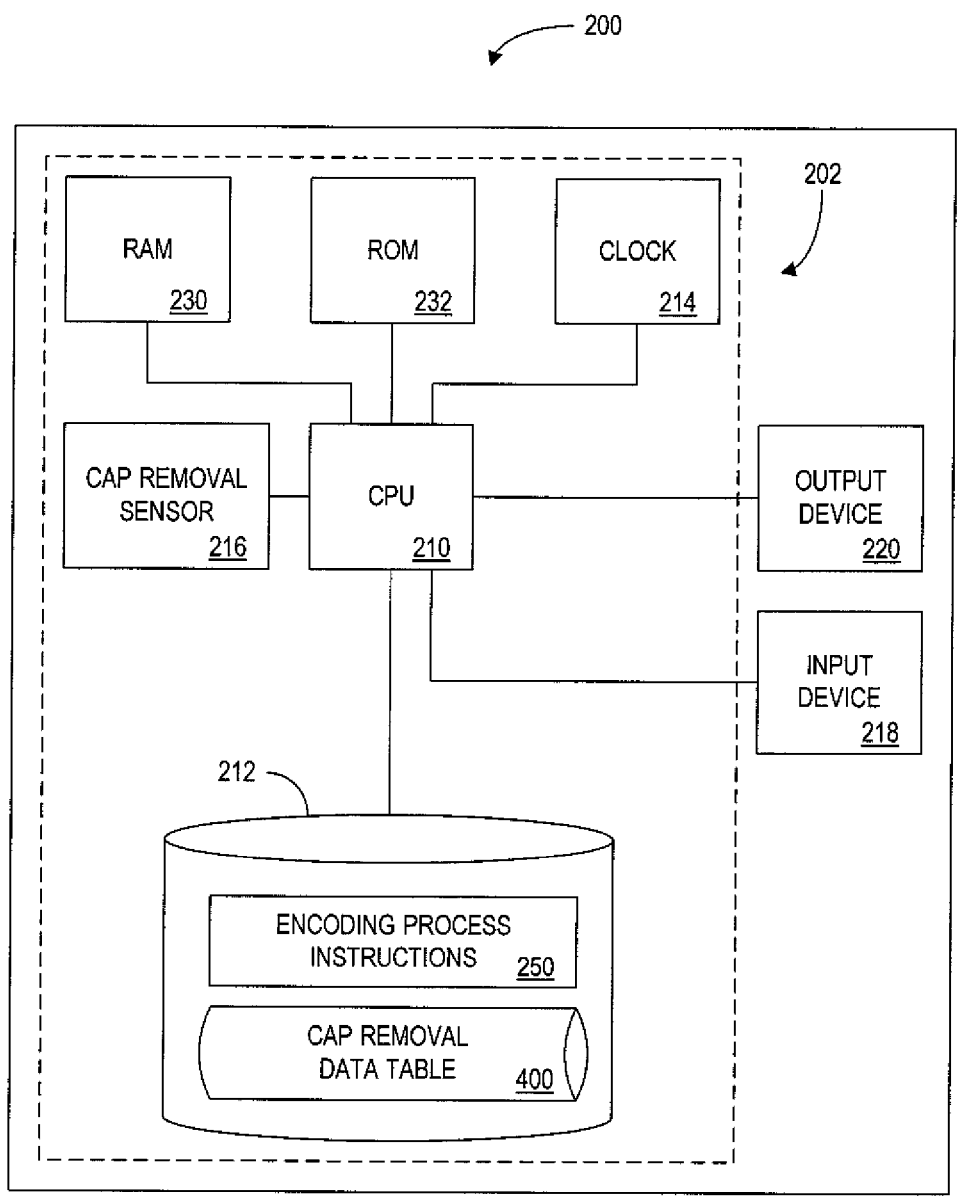
FIG. 2 is a schematic block diagram illustrating the components of the documenting module of the system of FIG. 1.
Figure 3:
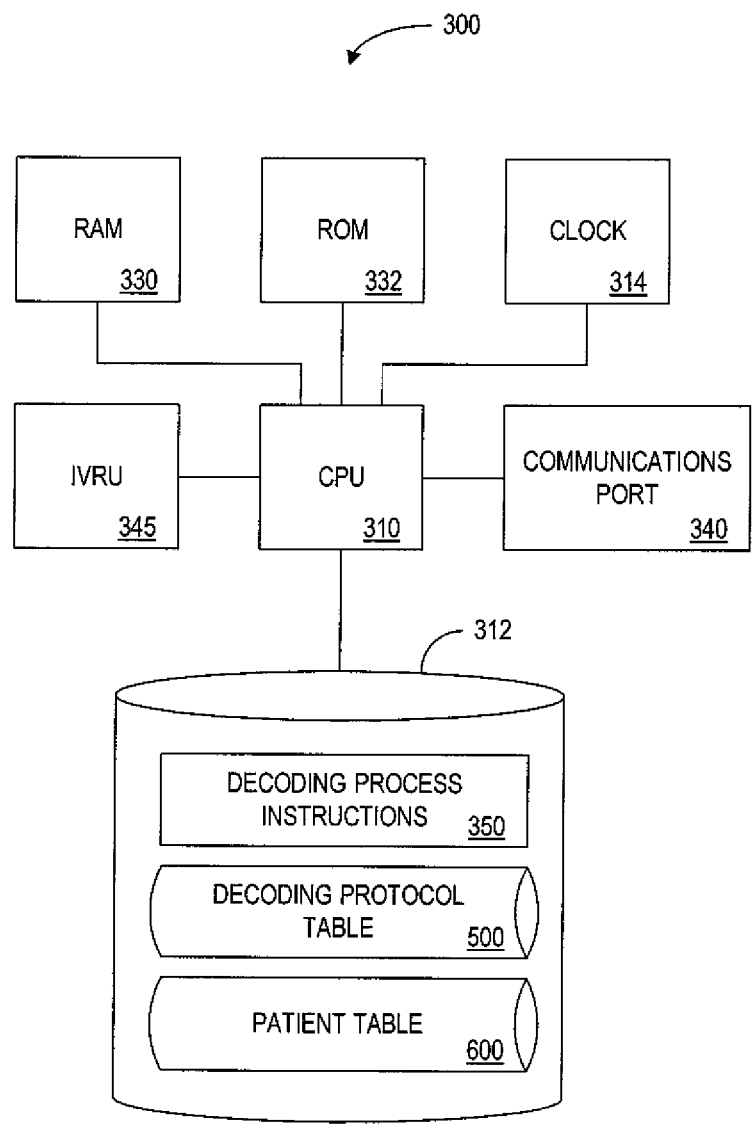
FIG. 3 is a schematic block diagram illustrating the components of the central controller of the system of FIG. 1.

An embodiment of the apparatus of the present invention will now be discussed with reference to FIGS. 1-3. FIG. 1 illustrates one exemplary system employing a documenting module 200 configured to measure and encode cap removal data generated by a user 116, and report the encoded data to user 116. The system further employs central controller 300 to receive the encoded cap removal data from user 116 via network 118. In one embodiment, network 118 is the public switched telephone network allowing the user 116 to communicate with central controller 300 via a standard telephone. Other suitable networks include local area networks ("LANs"), wide area networks ("WANs"), Intranets, the Internet, and the like. Such communication networks could also be wireless, allowing for cellular, infrared, or radio frequency ("RF") communications. FIG. 2 provides a more detailed illustration of documenting module 200 shown in FIG. 1. FIG. 3 provides a more detailed illustration of central controller 300 depicted in FIG. 1.

In a preferred embodiment, documenting module 200 includes elements incorporated within the cap of a prescription medication container, although it could also take the form of an add-on module attached to either the medicine bottle cap or bottle. Documenting module 200 could also be used in conjunction with a pill dispensing device that is operated to vend pills. A system that was capable of holding a plurality of prescriptions could also incorporate the documenting technologies of the present invention.

In operation, a user employs documenting module 200 to measure and document the number of times that an openable or reclosable cap, lid, or other similar dispensing covering has been removed from the associated pill container. The container is equipped with a detector which generates a first electrical signal in response to the opening of the dispensing covering and alternatively a second electrical signal in response to the reclosing.

In accessing the pill container by removing or replacing the cap, user 116 causes cap removal data to be generated which is stored as a numeric value. This cap removal data may be the total number of times that the cap has been removed in a given time period, the number of days in which the cap was removed more than once, the number of days in which the cap was not removed, the average number of removals per day, etc. It should be noted that the same measures may apply equally to cap replacement data which is similar to cap removal data in that both indicate the number of times that the container was accessed. In addition to recording the quantity of removals, documenting module 200 may store chronographic data regarding the timing of the removals. Such chronographic data may include the date/time of each removal, the average time of day of all removals over a particular period, the average number of hours between each removal, etc. Documenting module 200 receives the cap removal data from cap removal sensor 216, and encodes the data, thereby generating encoded cap removal data. In the simplest embodiment, the encoded cap removal data is an encoded version of the cap removal data, but in preferred embodiments, it may additionally incorporate a user identifier, drug identifying data, a cap identifier, an insurance policy identifier or other pertinent information such as biometric data or a timestamp.

The encoded cap removal data is displayed to user 116, as illustrated by reference numeral 120. This encoded data may take the form of a series of numeric digits or alphanumeric characters/digits. For example, the user may view a ten digit number representing the encoded data and type these digits into the keypad of his phone while connected to the central controller 300 via an interactive voice response unit ("IVRU"). The user might alternatively read out the digits of the encoded cap removal data to a human operator.

Central controller 300 decodes the received encoded cap removal data and stores the decoded information. A third party may employ central controller 300 to determine and authenticate the number of times the user 116 removed the cap, thereby providing greater assurance that the user has consumed the prescribed medication. Such compliance data could be used to lower insurance premiums in much the same way that motorists are rewarded with lower car insurance premiums for wearing safety belts.

Referring now to FIG. 2, the components of documenting module 200 are illustrated. Documenting module 200 includes a central processing unit ("CPU") 210, such as a Pentium Processor manufactured by INTEL or the like. CPU 210 receives input from a number of sources including clock 214, cap removal sensor 216, random access memory ("RAM") 230, read only memory ("ROM") 232, input device 218, output device 220, and data storage device 212. Clock 214 maintains an internal representation of the time/date and may be used to provide a timestamp that may augment the cap removal data. Clock 214 may be used to track time of day, date, day of week or any other well known chronographic measurement.

Cap removal sensor 216 supplies CPU 210 with an indication of the number of times that the cap has been removed and/or replaced. This sensor could take many forms. In one embodiment, a switch is used which is physically engaged when the top is placed on the pill container and which is disengaged when removed. Other functionally equivalent magnet switches or the like could be used so long as they give an accurate indication of a parameter representing the opening and closing of the pill container. The cap removal parameter generated by cap removal sensor 216 may represent one of a number of measurements. The cap removal data may include, for example, the number of cap removals in a particular period, the date and time of each of the last twenty removals, the number of pills dispensed over a given period of time, etc. For examples of cap removal sensors, those of ordinary skill in the art may refer to U.S. Pat. No. 4,939,705 to Hamilton, et al., the entirety of which is incorporated by reference herein.

Another pill dispensing sensor technology that may be used in the present invention is described in U.S. Pat. No. 4,616,316 to Hanpeter et al., also incorporated by reference herein. The device of Hanpeter consists of a blister pack with an array of plastic blisters which define compartments for medication. The backing sheet has conductive traces which are respectively ruptured when the medication doses are removed. An electronic memory circuit detects the ruptures and stores the data over a period of time, performing a function similar to the cap removal sensor 216 of the present invention. Those of ordinary skill in the art will appreciate that any pill access sensing technology which is capable of generating an electronic signal may be used as cap removal sensor 216.

Input device 218 may be employed by CPU 210 to receive external input such as a user identifier, a cap identifier, an insurance policy identifier, or a prescription identifier. A number of alternative devices may be employed to perform the function of input device 218. Input device 218 may be a numeric keypad for receiving input from a user. Alternatively, a biometric device, such as a fingerprint or retinal scanner could be employed as input device 218. Further, input device 218 could be a magnetic card reader or smart card reader for receiving data from a card carried by a user. If input device 218 is a smart card reader, it may also operate as an output device to transmit an encoded measurement value to an associated smart card. Input device 218 might also incorporate speech recognition software so as to allow users to enter their user identifier via voice. Those of ordinary skill in the art will appreciate that many forms of input may be used.

CPU 210 is also configured to output data via output device 220. Output device 220 is preferably a liquid crystal display ("LCD") unit, light emitting diode ("LED") or other conventional display unit that may be used to visually communicate information to user 116. This data may be represented as numeric or alphanumeric characters, or could take the form of a barcode or pulsed light display. Numeric characters could scroll slowly across a screen of output device 220 allowing for a large number of characters to be displayed with a relatively small viewing area. Output device 220 could include one or more speakers to facilitate audible transmission to the user, allowing the user to simply hold up a telephone to the output device after a connection was made to central controller 300 for DTMF transmission of the encoded cap removal data. In another embodiment, output device 220 includes a printer or memory device for permanently recording output. Output device 220 could also incorporate standard contacts for communication with smart card devices.

CPU 210 is also connected to RAM 230 and ROM 232 for temporary and long-term storage requirements, respectively. ROM 232 could store cryptographic keys used to encode cap removal data, as well as a cap identifier which uniquely identifies the cap. Such a cap identifier may be encoded along with cap removal data before it is displayed to user 116, allowing central controller 300 to authenticate the source of the cap removal data.

CPU 210 is further configured to access data storage device 212. Data storage device 212 stores cap removal data table 400 which is described more fully with reference to FIG. 4. Storage device 212 also includes instructions for implementing the documenting steps of the present invention as described with reference to FIG. 7. Included within storage device 212 are encoding process instructions 250 which are the protocols used in encoding cap removal data. These instructions are executed by CPU 210, although a separate encoding processor could be employed in conjunction with CPU 210. Storage device 212 may store one or more cryptographic keys used in this encoding process, with a corresponding cryptographic key stored within data storage device 312 of central controller 300. Storage device 212 is preferably flash RAM, although it could also be a combination of RAM and ROM, optical disk drive, RAM drive or any other conventional storage device as would be deemed appropriate by one of ordinary skill in the art. Flash RAM has the advantage of consuming a small amount of space and being capable of storing data even when power is interrupted.

Data storage device 212 may also store prescription data such as the number of doses contained in that particular pill container or the desired time windows within which the drugs are to be consumed. This data could also be stored in RAM 230 or ROM 232.

Data storage device 212 is also preferably capable of being updated periodically as new prescriptions are obtained. User 116 may thus obtain a documenting module 200 which can be attached to pill containers that are discarded after use. Each time the user goes back to the pharmacy he is provided with a new pill container and new pills. The user brings documenting module 200 so that data and software stored in storage device 212 may be updated. In this way, revised prescription data may be conveniently entered.

In order to physically secure documenting module 200, secure perimeter 202 may be employed to protect the elements responsible for generating the encoded cap removal data. Such a secure perimeter could provide tamper detection signals to CPU 210 for use with encoding process instructions 250, as discussed more fully with reference to FIG. 6. In one embodiment, secure perimeter 202 is a resin or similar substance applied to the indicated elements which is allowed to harden to form a protective shell. Any attempt to remove one or more chips from within the resin results in destruction of the chip or the loss of data.

Power requirements of documenting module 200 could be supplied through batteries, AC/DC adapter, or solar cells. A lithium battery (not shown) could supply small voltages to the components of documenting module 200. AC/DC adapters may be used for those embodiments in which substantial power is needed for display or other purposes.

Referring now to FIG. 3, the components of central controller 300 include CPU 310, clock 314, RAM 330, ROM 332, communication port 340, Interactive Voice Response Unit ("IVRU") 345 and data storage device 312. Clock 314 is operatively connected to CPU 310 for maintaining and providing a chronographic measurement, such as time and date. Such measurements may be useful in establishing an audit trail for documenting the communications received from user 116. Communication port 340 is operatively connected to CPU 310 for transmitting and receiving data over network 118. In the preferred embodiment, communications from user 116 may be received through IVRU 345 so that a simple phone call can be used for quick and efficient transmission of encoded cap removal data. Such an embodiment allows the user to transmit data without having a modem or direct connection, allowing for off-line transmissions. In another embodiment, communication port 340 may interface CPU 310 to an I/O device controllable by a human operator or a smart card reader, allowing user 116 to download cap removal data onto a smart card which is then presented to a third party (such as a local pharmacist) with direct communication links to central controller 300.

Data storage device 312 is operatively connected to CPU 310 providing storage for and access to process instructions and data. Data storage device 312 stores decoding protocol table 500 and patient table 600, described more fully with reference to FIGS. 5 and 6, respectively. Storage device 312 further includes decoding process instructions 350, for implementing the steps of the present invention as described below with reference to FIG. 8. Storage device 312 could take the form of a conventional disk drive employing magnetic media, a CD or DVD drive, optical disk drive, RAM drive or any other conventional storage device as would be deemed appropriate by one of ordinary skill in the art.

CPU 310 is operatively connected to RAM 330 and ROM 332 for temporary and permanent storage requirements, respectively. ROM 332 could store cryptographic keys used to decode cap removal data.

Data Tables

Figure 4:
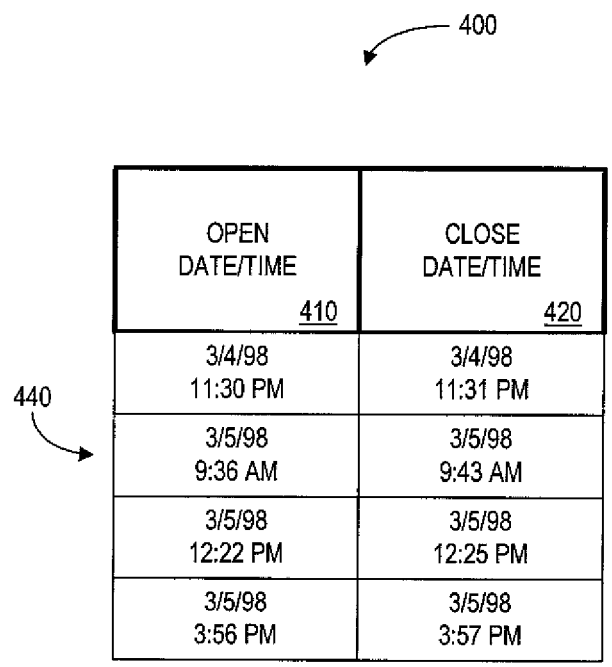
FIG. 4 depicts an exemplary cap removal data table stored in the memory of the documenting module.
Figure 5:
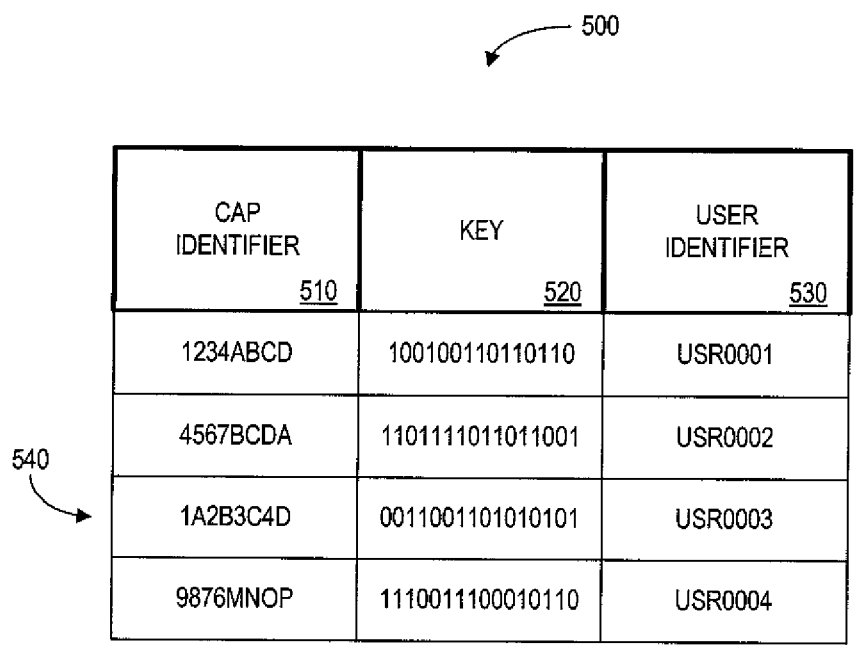
FIG. 5 depicts an exemplary decoding protocol table stored in the memory of the central controller of FIG. 3.

Referring now to FIGS. 4 through 6, the data tables associated with an exemplary embodiment of the present invention will be described. According to one exemplary embodiment, a health insurance provider employs the present invention to reward policy holders with lower premiums in the event that they comply with the instructions of the prescriptions provided to them.

FIG. 4 illustrates the contents, in tabular format, of an exemplary cap removal table 400 of documenting module 200. Cap removal table 400 provides a log detailing the usage of a particular prescription, storing data generated by cap removal sensor 216. Each record of cap removal table 400 corresponds to a particular cap removal event, and includes an open date/time 410 and a close date/time 420. Open date/time 410 and close date/time 420 represent the beginning and ending times of the corresponding cap removal, respectively. Other types of chronographic data may be stored as described above. The number of records in cap removal table 400 indicates the number of times that the cap has been removed from the pill container. Records of the table may be aggregated to form weekly or monthly totals.

The exemplary cap removal table 400 includes four records. Record 440 represents a cap removal event which occurred on Mar. 5, 1998, with the cap opened at 9:43 AM and replaced at 9:36 AM. The cap removal data is stored in field 410 when the cap is removed (opened) and is stored in field 420 when the cap is replaced (closed). One of the advantages to storing the times of access is that some medications are much more effective at certain hours of the day, making documented cap removal data much more valuable to a third party. Data stored with data table 400 may be periodically deleted by CPU 210 if storage space is constrained.

Referring now to FIG. 5, there is illustrated an exemplary decoding protocol table 500 of central controller 300. Each record of decoding protocol table 500 stores data associated with a particular documenting module 200. The contents of cap identifier field 510 uniquely identify each record of table 500. Key field 520 stores one or more keys used by that particular documenting module 200 to encode/decode cap removal data. Although key field 520 shows a plurality of keys, those of ordinary skill in the art will appreciate that a single universal key could be used for each documenting module 200. In such an embodiment, the universal key might be stored in ROM 332. User identifier field 530 represents the user assigned to that particular cap identifier. Such data could be registered by the user via communications port 340 or could be received from the pharmacy which filled the prescription. The user identifier could also be assigned by central controller 300.

Record 540 of decoding protocol table 500 represents a particular cap with an identifier of "1A2B3C4D." This cap has an associated key 520 of "0011001101010101" which corresponds to user "USR0003."

Referring now to FIG. 6, there is illustrated an exemplary patient table 600. Each record of patient table 600 represents data associated with particular patient. User identifier field 610 stores data representing the purchaser or user of the pill container. Those of ordinary skill in the art will appreciate that the user identifier could be the user's name, social security number, policy number, password, PIN, etc. User name field 620 stores his or her name. Address field 630 stores the street address of the user, while phone number field 635 identifies a contact phone number for the user, allowing central controller 300 to call the user to request encoded cap removal data. Policy identifier field 640 is used in those embodiments in which discounts may be applied to a user's policy. Account identifier field 650 identifies a financial account such as a credit card number or checking account number. This account could be used to reward or penalize the user 116 based on the received cap removal data.

In one embodiment, user compliance may be authenticated through the decoding of the received encoded cap removal data. The user may be rewarded with a discounted monthly insurance premium to reflect the lower expected probability of future complications. Other rewards could include a fixed discount off of future prescriptions, or a decrease in the amount of the deductible for hospital visits associated with the condition for which the drugs were prescribed.

Tampering indication field 660 stores an indication of whether or not secure perimeter 202 has been breached. This tampering indication is generated by CPU 210 and transmitted to central controller 300 via encoded cap removal data.

The exemplary patient table 600 includes four records. Record 670 stores information about the user "JOHN SMITH" whose user identifier is "456123." Address field 630 indicates that he lives at "22 RIVER PL. METROPOLIS, USA" and that his phone number is "(345) 123-4567." He has an insurance policy identified as "POL0002" and has an account identifier of "6011-2468-9090-1048" for use in those embodiment requiring billing or the provision of rewards. Field 660 stores an indication that there has been "NO" tampering detected.

Apparatus Operation

Having thus described the architecture and components of the present invention, the operation of documenting module 200 and central controller 300 will now be described in greater detail with reference to FIGS. 7 and 8, and continuing reference to FIGS. 1-6.

Figure 7:
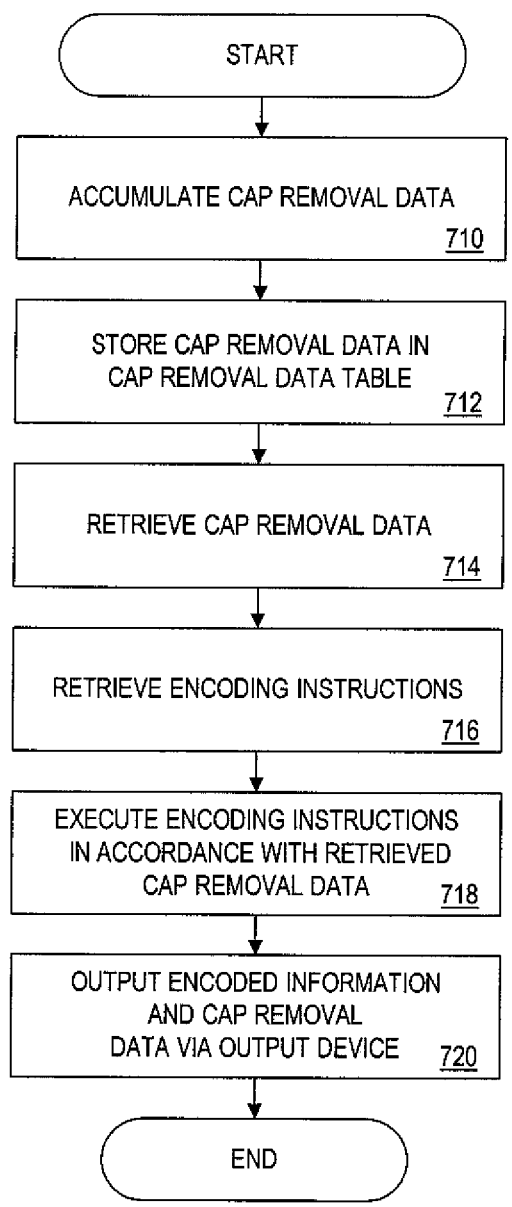
FIG. 7 is a flowchart illustrating the computer-implemented process steps enabling a user to document cap removal data.

Referring now to FIG. 7, a flowchart is presented illustrating the process steps implemented by CPU 210 of documenting module 200. At step 710, CPU 210 accumulates data indicating that the cap has been removed by receiving signals from sensor 216, a switch which is physically engaged when the top is removed or replaced. Sensor 216 could generate data for both removals and replacements, or it could be limited to sensing only removals or only replacements. At step 712, this data is stored in cap removal data table 400. In a preferred embodiment, data regarding every cap removal is stored, although data could of course be selectively stored if memory limitations were a constraint. For example, every fifth cap removal could be stored or every cap removal occurring between the hours of 2:00 PM and 6:00 PM. In another embodiment, cap removal data represents only an indication of whether or not the cap has been removed within the parameters described by the prescription. Thus, data storage device 212 of documenting module 200 stores a positive value if the patient has removed the cap once every day between the hours of 3:00 PM and 9:00 PM, and stores a negative value if one or more days have elapsed in which the cap was not removed within this window. Sensor 216 could also transmit cap removal data to CPU 210 only a fixed number of times within a given period. For example, the maximum number of transmitted cap removals within a twenty-four hour period might be two. Such a restriction would make it impossible for a user to generate false cap removal data by repeatedly opening and closing the cap within a short period of time. A user with a month long prescription, for example, might realize at the end of the month that he had forgotten to take his medication. Trying to generate a month's worth or cap removal data would be futile since only two cap removal events would be recorded within each twenty four hour period. Although described as being stored in cap removal data table 400, those of ordinary skill in the art will appreciate that cap removal data could alternatively be stored in RAM 230 or some other type of chip based memory within documenting module 200.

At step 714, this stored data representing a measurement of the number of cap removals is retrieved by CPU 210. In one embodiment, CPU 210 retrieves the number of records within cap removal data table 400 in order to determine the number of times that the cap has been removed. For many prescriptions, this will be a number ranging from ten to a hundred, depending on the period of time covered. CPU 210 next retrieves encoding process instructions 250 from data storage device 212 at step 716. These instructions are executed at step 718 and applied to the cap removal data retrieved at step 714. For example, if the number of cap removals is "36" the resulting encoded cap removal data may be "3489112073." The advantage of encoding the cap removal data is that the user is not able to lie about the number of cap removals when presenting the data to a third party. Without knowing the encoding protocols, the user does not know the encoded equivalent of any set of cap removal data, thus preventing the user from fabricating false cap removal data. Although the user could simply make up a number to represent false cap removal data, the probability that it represented a reasonable number of cap removals when decoded would be made vanishingly small.

The instructions of step 718 may direct CPU 210 to perform any type of encoding commonly used to render data secure. Examples include symmetric key encryption, public key encryption, hash algorithms, digital signatures, and the like. If lower levels of security are required, substitution ciphers or transposition ciphers may be appropriate. Common types of encoding are described in "Applied Cryptography, 2nd Edition" by Bruce Schneier, 1996.

Although step 718, as illustrated, represents the steps required to encode the number of times the cap has been removed, it may also include steps for encoding other data in addition to the cap removal data, including the user identifier, the cap identifier, a beginning timestamp and an ending timestamp. The user may also enter the number of pills that he takes at each cap removal event, entering the information into input device 218. In one embodiment, a cap identifier is stored in ROM 232 of documenting module 200. CPU 210 retrieves this cap identifier and concatenates it with the cap removal data retrieved at step 714. The resulting combined data is then encoded as described above. The advantage of this embodiment is that when the encoded cap removal data is decoded by central controller 300, the identity of the cap may be authenticated in addition to the number of cap removals, preventing a user from providing the encoded cap removal data from another user's documenting module 200. The encoding process of step 718 may also incorporate results from an integrity test of secure perimeter 202. Should CPU 210 detect that the secure perimeter had been breached, an indication is concatenated with the cap removal data prior to the encoding process. Decoding by central controller 300 then reveals evidence of the breach.

The retrieval of cap removal data at step 714 and the subsequent encoding at steps 716 and 718 may be scheduled to occur at prescribed dates, such as the first day of each month or the date at which the prescription is scheduled to run out. The steps may also be performed upon request by user 116. In this embodiment, the user actuates a button of input device 218 of documenting module 200, the actuation signaling CPU 210 to perform the encoding operation.

At step 720, CPU 210 outputs the encoded cap removal data. The step of outputting the encoded cap removal data may be performed in a number of ways. In a preferred embodiment, the encoded cap removal data is output via output device 220 for viewing by the user. The user may then initiate a phone call to IVRU 345 of central controller 300 and type in the displayed encoded cap removal data using the touch tone keys of his telephone. Such a process has the advantage of simplicity and low cost. No modem or online connection is required. Users may be entered into sweepstakes drawings every time that they call in with encoded cap removal data, encouraging greater participation rates. The probability of winning the sweepstakes could even be based partly on the degree to which the user complied with the prescription instructions.

Input device 218 could incorporate a switch or button, actuated by user 116 to control the display of output device 220. Such an embodiment would allow the user to select whether to view the cap removal data in encoded or non-encoded form.

In an alternate embodiment, the encoded cap removal data may be output to a smart card or magnetic stripe card via an appropriate interface (not shown). The user could insert a smart card into an electrical contact of output device 220, initiating the transfer of data to the smart card. This smart card could then be mailed to the central controller 300 for decoding, or inserted into a reader device (such as a kiosk) at a hospital or pharmacy for later transmission to central controller 300.

It should be noted that the functionality of step 720 may include outputting data in addition to the encoded cap removal data. For example, the user identifier, a beginning timestamp and an ending timestamp may be output in either an encoded or non-encoded format. As described with respect to the encoded cap removal data, the step of outputting may be accomplished via output device 220 or an appropriate smart card or magnetic stripe card interface.

Figure 8:
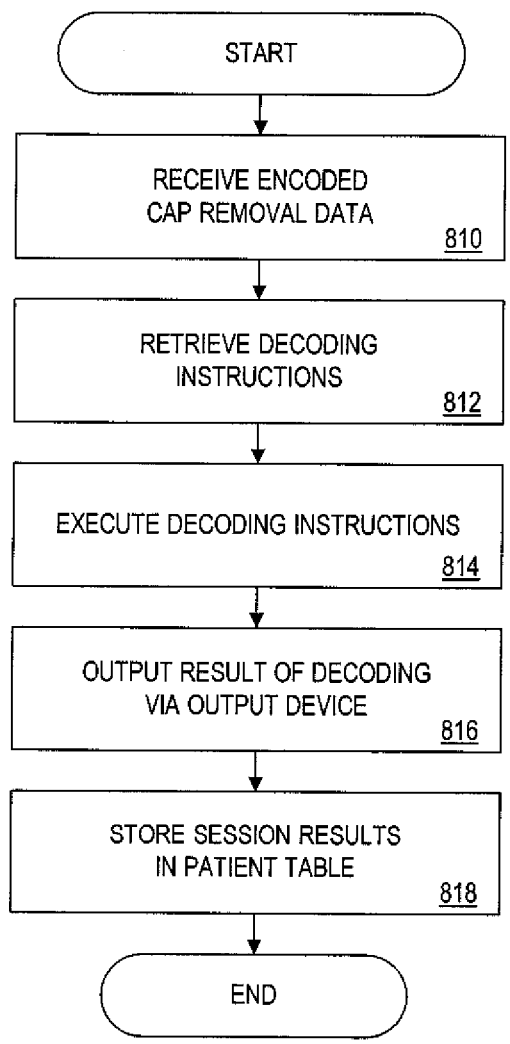
FIG. 8 is a flowchart illustrating the computer-implemented processes steps enabling a third party to authenticate cap removal data.

Referring now to FIG. 8, a flowchart is presented illustrating the computer implemented process steps of authenticating the received encoded cap removal data. At step 810, central controller 300 receives the encoded cap removal data, user identifier and cap identifier from user 116. Preferably, the encoded cap removal data is transmitted by the user via IVRU 345, however the user may alternatively employ a smart card or equivalent device which may be physically delivered to an operator of central controller 300. In the preferred embodiment, the encoded cap removal data may also include additional encoded information such as a beginning timestamp, an ending timestamp, a secure perimeter test result, or a diagnostic test result as described with reference to FIG. 7.

At step 812, central controller 300 retrieves decoding process instructions 350 from data storage device 312 and then executes these instructions at step 814 to decode the received cap removal data in order to derive a parameter indicative of the decoded cap removal data. In the preferred embodiment additional data may be derived from the encoded cap removal data. According to the preferred embodiment, step 814 includes the steps of deriving a beginning timestamp, an ending timestamp, the secure perimeter test result or a diagnostic test result.

For those embodiments in which cap removal data is encoded by calculating a hash value associated with the cap removal data, central controller 300 executes decoding process instructions 350 to apply the same hash algorithm to the cap removal data to determine the associated hash value. If the two hash values are the same, the cap removal data has been authenticated.

At step 814, central controller 300 may additionally determine whether the secure perimeter of documenting module 200 has been breached. Although this determination may be effected in a number of conventional ways, in the present embodiment, the determination is made based on the secure perimeter test result decoded at step 814. If central controller 300 determines that the secure perimeter has been breached, central controller 300 is directed to store an indication within the tampering indication field 660 of patient database 600.

At step 816, CPU 310 outputs the result of decoding step 814 to the user, providing immediate feedback as to the documented cap removal data. This output may be in audio form, provided via IVRU 345 or communications port 340. The decoded cap removal data is then stored at step 818 in patient table 600.

CPU 310 may additionally update user data stored within data storage device 312 based on the decoded cap removal data. For example, a user record may be flagged to indicate that the patient had not complied with the instructions of his prescription, or that he had complied with only the bare minimum required. Historical user data such as this could provide the basis for rewards or penalties, and could serve as a basis for making pricing decisions for future insurance coverage. Users might be provided with higher reimbursement levels for drugs for which they had complied with the prescription instructions. For example, a user might pay $100 for a prescription, with the insurance provider reimbursing one quarter of that amount if the user does not comply with the prescription requirements, and one half of that amount if he does comply with the requirements. Insurance companies might also require that the user call in with encoded cap removal data before any reimbursements are provided.

It should also be recognized that documenting module 200 may include additional processing instructions to store cap removal statistics associated with a user, and may output an encoded cap removal code only upon reaching a predetermined reward threshold. Thus, encoding process instructions 250 could include code which outputs encoded data only when the user opens the pill container a number of times equal to the number of doses stored within the container.

A further application of the present invention enables a pharmaceutical supplier to offer rebates to purchasers of pharmaceuticals based on usage. Alternatively, a physician could provide a money back guarantee provided a user conforms with the prescription for a specified period of time.

Yet another application of the present invention enables medical service providers such as doctors, health maintenance organizations and insurance companies to offer preferred rates to their clients who consistently follow prescription instructions. By employing the present invention, any medical service provider may verify prescription compliance.

The disclosed method and apparatus for authenticating cap removal data may be applied to a number of commercial applications. For example, drug testing trials commonly involve dispensing drugs to a number of test subjects. These subjects are monitored to determine the efficacy of the drug, with the results provided to a governing authority such as the Food and Drug Administration for approval. Subjects who do not take the medication according to the prescribed schedule will of course negatively impact the results, so drug companies could use the authentication procedure of the present invention to eliminate bad data from the study.

In some embodiments, the documenting module 200 (or processor thereof) and/or central controller 300 (or processor thereof) may determine a compliance status (i.e., "compliant" or "not compliant"). Such a compliance status may be determined, for example, for a particular user, particular medication, and/or particular unit of time. The compliance status may be determined based on cap removal data. In one example, the status for a user may be determined as "compliant" if the cap removal data associated with the user indicates the user has met a required minimum number of cap removals per unit time.

In one or more embodiments, once a compliance status has been determined, the documenting module 200 may output an indication of compliance status. For example, if a user is not compliant, a warning indication or other message may be output via an output device. For example, if a user fails to remove the cap of a pill bottle once during a 12-hour time period, a red LED associated with the pill bottle may be actuated at the end of the period. Other exemplary warning indications include an audio speaker emitting sound (e.g., "beeping"), an LED display or LCD screen displaying text (e.g., "Please Take Your Pills"), etc. In one or more embodiments, such warning indications may persist until the next cap removal.

In some embodiments, the number of cap removals per a specified period of time may be recorded (e.g., one or more appropriate fields of a cap removal data table such as table 400 may be updated). For example, if a user must take one pill every 24 hours, each 24-hour time period during which a cap has been removed at least once may be recorded as a "success" (i.e., the user was compliant), while each 24-hour period during which a cap was not removed may be recorded as a "failure" (i.e., the user was not compliant).

In some embodiments, stored rules may indicate to output a warning indication based on the number of recorded failures. For example, a warning indication may be output each time a failure is recorded. In another embodiment, a warning indication may be output if a user's "failure percentage" (i.e., the number of failures divided by the number of elapsed time periods) is equal to or greater than a predetermined percentage amount (e.g., 0.15 or 15%).

In one or more embodiments, a user may be penalized based on a number of failures (e.g., a threshold number of failures is reached). For example, a penalty may be a removal of a previously awarded discount or an increase in a co-pay for prescriptions. In another embodiment, a user may be penalized by not having a game result displayed (display of game results as a benefit are described in more detail below).

In one or more embodiments, a user may be provided with one or more benefits based on a number of recorded successes, a percentage of recorded successes, and/or a ratio of recorded successes to recorded failures. As described above, a user may be provided with an encrypted code that may be used to redeem one or more benefits. For example, a user acquiring 100 consecutive successes may be provided with a code that may be entered into a Web site to achieve a discount on goods or services offered by the Web site. In another example, a user may be provided with a code entitling the user a number of entries in a sweepstakes. For example, for every five successes, the user may be provided with an encrypted code, which the user may "call in" to a sweepstakes telephone service. Alternately, at the end of every month, a user may be provided with a number of benefits (e.g., sweepstakes entries) based on a "success percentage" (i.e., the number of successes divided by the number of elapsed time periods). In one embodiment, the value of a benefit (e.g., discount amount, sweepstakes jackpot, etc.) may increase relative to the number of a user's successes.

It should be noted that a code may be not be encrypted, but scrambled in some other manner (e.g., the sum of all the digits of the code 102311 is less than ten, and the code is therefore valid). In some embodiments, codes may not be encrypted, scrambled, encoded or otherwise secured at all.

In one or more embodiments, a benefit may comprise a set of lottery numbers. For example, so long as a user is compliant, the user may be provided with several numbers every week for a state-drawn lottery. The numbers may be output, for example, via an output device associated with the medicine container. In one example, an LED screen depicts five lottery numbers, as well as the date/time of the drawing and an encrypted code, which represents the date and the lottery numbers displayed to the user. Should the numbers be winners, the user may provide the encrypted code to a lottery agent so that the claim to winnings is validated. In another example, a medicine container may further comprise or be associated with a printer that may function to print a physical lottery ticket.

In one or more embodiments, the user may be allowed to select their own lottery numbers for a drawing. For example, in one embodiment the medicine container may output a code, whenever the user is eligible for an entry into a lottery drawing. The user may use the code to access a Web site, via which the user may select a set of lottery numbers. The Web site may first decrypt the code to verify that the user is in fact eligible to select the set of lottery numbers. In another example, a user may provide a set of preferred lottery numbers to the medicine container or to another entity (e.g., a pharmacist may download the selected numbers to the medicine container or the user may register, with the central controller, the selected set of numbers as associated with the user via a Web site or other connection). In this latter example, whenever the user is eligible to be entered into a lottery drawing, the user may be provided with a code. The user may then call in this code to the central controller or input it to a Web site in order to have his preferred set of lottery numbers automatically entered into the next available lottery drawing. Alternatively, the medicine container may be operable (e.g., via a modem) to communicate with the central controller whenever the user becomes eligible for an entry into a lottery drawing, in order to transmit to the central controller an indication of the user's eligibility. Upon receiving such an indication, the central controller may automatically enter the user's preferred set of lottery numbers into the next available lottery drawing.

In or more embodiments, a medicine container (e.g., the documenting module 200 of the medicine container) comprises a random number generator. In one such embodiment, each cap removal may trigger the generation of a random number. A benefit may then be awarded based on one a result associated with the random number (e.g., "You've won a Ford Explorer! Call 1-800-555-5555 and enter code 205034059"). In one embodiment, the random number itself may be displayed to the user. The user may then determine the result associated with the random number by calling an entity such as the central controller 300 with the random number and/or by visiting a Web site that displays the results associated with various random numbers. In another embodiment, the result associated with the random number may be displayed via an output device associated with the medicine container.

The data table comprising a list of random numbers and their corresponding results may be stored in a memory of the medicine container or another processor responsive to instructions from the medicine container. For example, the data table may be stored in the memory of a computing device (e.g., the user's PC onto which appropriate software including the table has been loaded) and the medicine container may include an infra-red (IR) or radio frequency (RF) based output device via which the computing device may be instructed to access the table and display the result associated with the random number. In another example, the user may manually enter the random number into a computing device (e.g., the user's PC onto which appropriate software including the table has been loaded), thus causing the computing device to display the result to the user.

It should be noted that a "result" may comprise a representation or indication of a benefit to be provided to the user. For example, a result may comprise a slot machine like collection of graphical symbols (e.g., cherry-cherry-cherry). A data table may store a plurality of available results and the benefit (if any) associated with each respective result. This data table may be stored, for example, within a memory of the medicine container, within the memory of another computing device (e.g., the user's PC onto which appropriate software including the table has been loaded), and/or the memory of the central controller 300.

A particular embodiment of the present invention will now be described with reference to FIGS. 9A and 9B. Applicants have recognized that many persons enjoy playing games and look forward to the moment at which the result of a game is revealed. For example, many persons enjoy playing games of chance such as slot machine games and greatly enjoy the moment when the reels of the slot machine stop along a payline to reveal the result of the game. Applicants have further recognized that taking medicine is typically not an entertaining or enjoyable experience, which is one of the reasons many people either forget or avoid taking their medicine in compliance with a prescription. Accordingly, Applicants have recognized that providing a game interface and revealing results of a game in response to the taking of a medicine will be a particularly powerful and effective method of motivating persons to take their medicine.

Thus, in accordance with one or more embodiments, a medicine container may include an output device for outputting the result of a game. In one embodiment, the result of a game may be output via an entertaining game interface, such as a slot machine interface. Having the result be output via a game interface will further enhance the user's enjoyment of obtaining the result of the game.

Figure 9A:
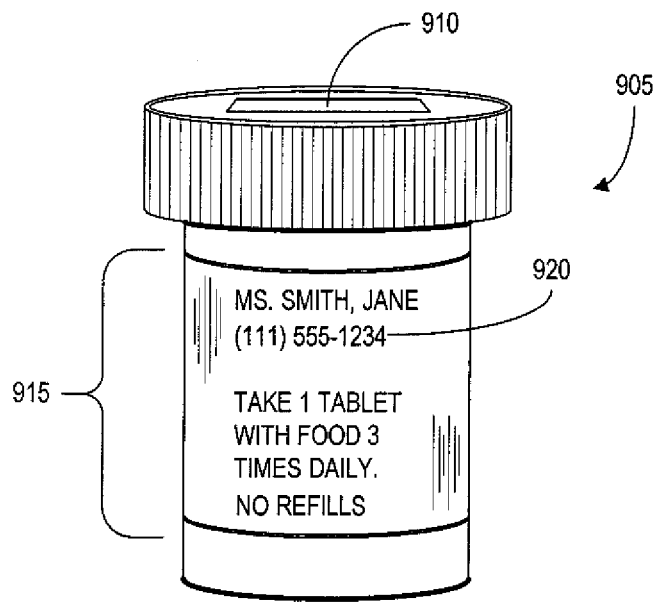
FIGS. 9A and 9B illustrate a schematic diagram of a pill bottle, in accordance with one or more embodiments of the present invention.

Referring now to FIG. 9A, a medicine container 905 includes a cap 910 and a cavity 915 for holding medicines. The cavity 915 may have attached thereto a label 920 that includes instructions for taking the medicine contained in the medicine container 905. For example, the label 920 may instruct the user to take one pill twice a day. The label 920 may further include additional information, such as the user's identifier, pharmacy contact information, the prescription identifier, and/or one or more telephone numbers for the user to call in order to obtain benefits in accordance with embodiments of the present invention. It should be noted that although the medicine container 905 is illustrated as a cylindrical shape, a container of any shape may be used. It should further be noted that, in one or more embodiments, the label 920 may function as an output device (e.g., the label may be comprised of material operable to output electronic messages, such as a flexible LCD or e-ink™).

As described above, in one or more embodiments the medicine container may include an output device via which a result of a game may be output to the user. The output device may be included in, for example, (i) the cap of the medicine container; (ii) the cavity of the medicine container; (iii) the label of the medicine container; (iv) another portion of the medicine container; (v) a peripheral device associated with the medicine container; or (v) a combination thereof. The output device may comprise an audio output device and/or a display device. Possible output devices include: a cathode ray tube (CRT) monitor, liquid crystal display (LCD) screen (a flexible or rigid one), light emitting diode (LED) screen, a printer, an audio speaker, an infra-red transmitter, a radio transmitter. A display device comprising the output device may be operable to display still images (e.g., "winner") or animated images (e.g., spinning slot reels).

Figure 9B:
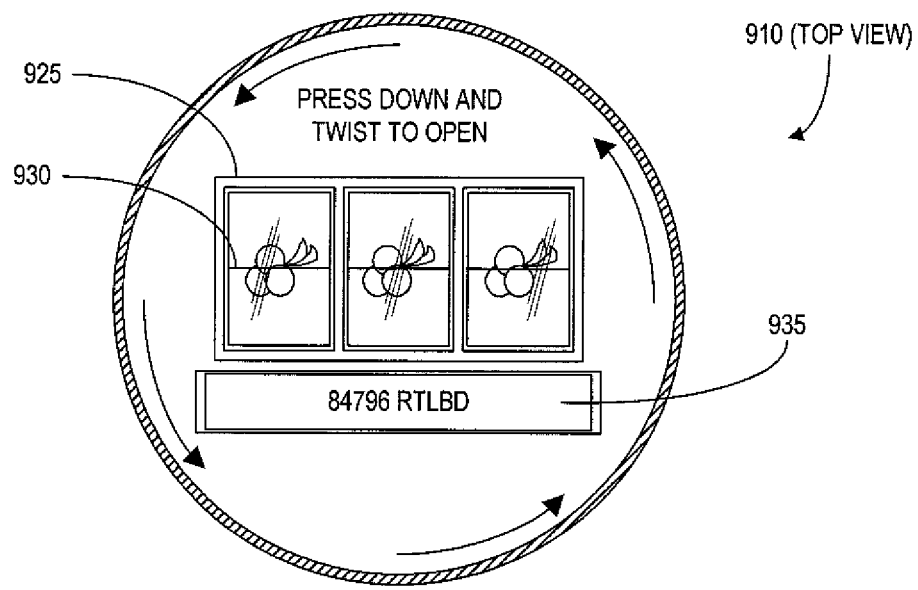

Referring now to FIG. 9B, a plan view of the cap 910 is illustrated. The cap 910 includes two display devices: (i) display device 925 and (ii) display device 935. It is understood that any number of display device can be used. In the embodiment of FIG. 9B, the display device 925 displays a representation of a result of a game via a slot machine interface. In the embodiment of FIG. 9B, the result of a game is represented by a plurality of symbols displayed along a payline 930, each symbol being displayed on the representation of a respective reel of a slot machine. It is understood that another interface based on another game or type of game may be used. The display device 935 displays additional information to a user. For example, the display device 935 may display a telephone number for the user to call, a description of a benefit to be provided to the user that corresponds to the result of the game displayed in display 925, and/or a code the user is to call in to the central controller 300.

In one embodiment, the user is provided with a chance to win a prize each time the user opens or re-closes the cap 910. In another example, the user may be provided with a chance to win a prize each time the user opens or re-closes the cap in compliance with the prescription (e.g., one every twelve hours, if the user is to take the medicine once every twelve hours). In such embodiments, the medicine container 905 may comprise a random number generator, a processor, a detector for detecting when the cap 910 has been removed and/or replaced, and a memory. The memory may store, for example, a probability table of available results (e.g., symbol combinations to be displayed via display device 925), each result corresponding to at least one random number that may be generated by the random number generator. In one or more embodiments, the memory may further store a payout table of available prizes, each prize corresponding to one or more results that may be displayed via display device 925.

Thus, for example, every time a detector of the medicine container 905 determines that the cap 910 has been removed (or, alternately, that the cap has been replaced), a random number generator included in the medicine container 905 (e.g., in the cap 910) may generate a random number. The processor of the medicine container 905 may then access the probability table to determine the result that corresponds to the random number and cause display device 925 to display the result. If the memory also stores a payout table, the processor may further access this payout table to determine the prize corresponding to the result and cause either display device 925 or display device 930 to display an indication (e.g., a graphical representation or textual description) of the prize. It should be noted that in some embodiments the user may separately be provided with a list of the prizes available, and the respective result that each prize corresponds to. For example, a user may be provided with a printed list of prizes and the one or more results corresponding to each prize or may be provided with access to a Web site on which this information is posted.

In either the embodiments where the medicine container 905 stores a payout table in memory or the embodiments where the user is provided with a list of prizes available, the prizes available to the user may be customized to the user or may be prizes generally available to all users participating in the system.

In one or more embodiments, random game results may be generated ahead of time (either by the medicine container or another computing device) and stored in the memory of the medicine container. In such embodiments, rather than generating a random number in response to a determination that a user has become eligible for a game result, the processor of the medicine container may simply retrieve a game result from memory and output it to the user. For example, the processor may retrieve the next available game result that has not previously been output to the user.

In one or more embodiments, the probability of winning a particular prize or the prizes available may change. For example, the longer a user is compliant with taking his medicine, the higher the probability of winning a prize becomes. In another example, more valuable prizes may become available as the user remains compliant over time. For example, the medicine container may store in memory information identifying the user and additional information associated with the identify of the user that may be used to determine the probability to be used in determining a game result for the user. Such information may include, for example, an indication of the user's current and/or past compliance with a cap removal requirement of a medication currently and/or previously associated with the user. In another example, such information may include an indication of the duration for which a requirement of the medication has been associated with the user (e.g., if the user has just begun a prescription, the user may be provided winning game results more frequently to encourage the user to become used to taking the medication as prescribed).

In one or more embodiments, the medicine container 905 may be operable to communicate with another computing device (e.g., the user's PC). For example, the user may download software that includes a game interface and that is operable to display game results based on information received from the medicine container 905. For example, the medicine container 905 may transmit to the PC a code or other instruction that causes the software on the PC to display a game result. The medicine container 905 may transmit such code or other instruction via, e.g., RF or IR signals, a cable connection between the medicine container 905 and the PC, or via the user, who may be instructed to manually input the information to the PC. In such embodiments, the medicine container 905 may not include a random number generator or table of game results in memory or be operable itself to display game results. Instead, the computing device may comprise these elements and be operable to perform these functions in response to input from the medicine container 905. In other embodiments, both the medicine container and the computing device may be operable to perform these functions and the user may select the method via which the game results are to be displayed (i.e., via the medicine container 905 or via the computing device).

In one or more embodiments, a user may be allowed to select one or more game interfaces or games via which results are to be displayed. For example, the medicine container may store more than one game or game interface in memory. In another example, the user may be instructed to visit a Web site that has downloads of various games and/or game interfaces available and may select one of these for download to the memory of the medicine container 905. In yet another example, the user may be asked to select a game or game interfaces (e.g., by a pharmacist) when the user takes possession of the medicine container or obtains a refill of medicine for the medicine container and this selection may be downloaded to the medicine container. In yet another example, different medicine containers 905 or medicine container caps

910 may be programmed with different games or game interfaces and the user may be provided with the appropriate one based on the user's selection of a game or game interface.

In one or more embodiments, to further motivate a user to take their medicine, the medicine container 905 may be programmed to initiate a game or begin the display of a game result at the times at which the user is supposed to take their medicine. Thus, for example, one of the representations of a reel may display symbol along a payline at a time the user is supposed to take the medicine. Additionally (or in lieu of beginning a game or the display of a result of a game), the medicine container 905 may be equipped with an audio output device and may output an audio signal to remind the user that it is time to take the medicine or that the game or display of a game result has begun. In some embodiments, the entire game result may be displayed at the time the user is supposed to take the medicine but the user may only be allowed to claim any prize that is associated with the result if the user had in fact opened and/or re-closed the medicine container before the full game result was displayed. This may further motivate a user to take their medicine in compliance with their prescription, since the user may be reluctant to chance a winning result being displayed and not being able to claim the corresponding prize.

In one embodiment, a result of a game may be displayed for a predetermined length of time (e.g., one hour) at a time the user is supposed to take his medication. For example, if the user is supposed to take his medication once every twenty-four hours and the last time the user opened the medicine container was 8:00 am yesterday, the medicine container may display a result of a game between 7:30 am and 8:30 am on the current day. If the user takes his medicine as he is supposed to, the user will be handling the medicine container during this one-hour period and will see the game result. Thus, if the game result is a winning one, the user will be able to claim the associated prize. If the user fails to take his medicine as he is supposed to, the user will miss seeing the game result displayed during the one-hour period. Many users will be motivated to remember to take their medicine as prescribed in order to avoid missing any winning game results.

In one or more embodiments, rather than being provided with a prize or a chance at a prize upon each opening or re-closing of the medicine container 905, the user may instead be building equity in a chance at a prize, improving his chance at winning a prize, or increasing the value of an available prize with each opening or re-closing of the medicine container 905. For example, in one game a user may win a prize if the user obtains a predetermined number of occurrences of a particular symbol over a plurality of game results (e.g., ten cherries). Thus, each time the user opens or re-closes the cap 910, the user is hoping to obtain a game result that includes a cherry. The medicine container 905 may be operable to track the number of occurrences of the particular symbol the user is attempting to collect. In such an embodiment, the frequency of the appearance of the symbol the user is attempting to collect may change. For example, the symbol may appear more frequently when the user first begins to collect the symbol, thus encouraging the user to comply with taking his medicine.

In another example, each time the user opens or re-closes the cap 910, the player may be provided with a chance to win a progressive jackpot for which the user is competing with other users of the system. Further, each time the user opens or re-closes the cap 910 a contribution to the progressive jackpot may be made, such that the progressive jackpot increases over time.

In yet another example, a discount or other benefit available to the user may increase over time as the user remains compliant. For example, a discount in the user's co-pay or insurance premiums may increase by a predetermined amount for each predetermined period of time over which the user remains compliant. In such embodiments the user may be penalized for not complying with a prescription by, for example, a substantial reduction or removal of such a discount. Thus, a user that has been compliant for an extended length of time and has thus earned a substantial discount will be quite motivated to remain compliant in order to maintain the level of discount that it took so long to build up.

In one or more embodiments, the user may be provided with a chance to win a prize each time the user opens or re-closes the cap 910 and also, in addition, be entered into a bonus game or pool for a chance to win a larger prize.

In addition to games of chance, the games playable by the user may include games of skill or games that are part chance and part skill. For example, a trivia game may be available to a user. The questions for the trivia game may be, e.g., stored in a memory of the medicine container 905 and/or the memory of another computing device (e.g., the user's computer) with which the medicine container 905 is operable to communicate.

In one example of a trivia game, the questions may be related to the medicine associated with a user (e.g., the medicine in the medicine container, another prescription associated with the user, or a combination thereof). For example, the user may be asked whether the medicine causes drowsiness, is to be taken with food, can be taken with alcohol, or is compatible with another medicine. In such trivia game embodiments, the medicine container may include an input device via which the user may provide answers to the questions.

In one or more embodiments, one or more trivia questions may be posed to a user as a further requirement of claiming a prize. For example, assuming a winning game result has been output to a user via the medicine container, the user may be required to visit a Web site in order to input an indication of the winning result (e.g., an encrypted code output along with the winning result) and claim the associated prize. However, before the user is allowed to claim the prize, the user may be asked one or more trivia questions. Such trivia questions may be related to one or more medicines the user currently has a prescription to or another medicine.

In another example of a type of game that may be played via a medicine container, an output device of the medicine container may output a number or set of numbers that the user must match to a second number or second set of numbers known to the user. For example, the user may win a prize if the number or set of numbers output via the medicine container matches the prescription number of a prescription associated with the user, the user's social security number, or the user's telephone number. Such a number or numbers output via the medicine container may be determined randomly in a manner similar to that described above.

In one or more embodiments, an input by the user may be incorporated into the determination of a game result, for added user enjoyment and further motivation to open the medicine container. For example, the exact time at which the user opens the medicine container may be incorporated into the determination of the random number used to determine the game result. For example, in one embodiment the random number generator may continuously generate random numbers and the random number generated at the time of the medicine container opening may be the random number used for the game result.

It should be understood that, as described at least with respect to FIGS. 9A and 9B, a user may not need to contact central controller 300 to determine whether or not they have won a prize. The result of the game may be displayed to the user via the medicine container 905 or via a computing device in communication with the medicine container 905. However, in some embodiments, the user may still need to contact the central controller 300 or another entity for further verification that the user is in fact entitled to the prize indicated by the game result. This may be particularly the case for prizes over a predetermined value (e.g., prize worth more than twenty dollars).

In one or more embodiments, a player may need to provide additional verification or validation of having taken the medicine as prescribed in order to collect a prize won based on a game result. For example, prizes valued above a predetermined threshold (e.g., twenty dollars) may require validation of compliance.

In one embodiment, validation of compliance may comprise having the user provide a code output by the documenting module 200, as described in detail above.

In another embodiment, a user attempting to win a large prize may be required to document compliance with a prescription by use of reagent test strips. For example, a user may be provided with a plurality of reagent test strips. A test area of each reagent test strip may be impregnated with an appropriate indicator that reacts with a particular substance being tested for. The medicine to be taken by the user may be coated with a quick-dissolving coating containing the substance being tested for. Alternatively, the user may be provided with a second set of pills, the second set of pills being coated or impregnated with the substance being tested for, or a syrup or other edible form that includes the substance being tested for. In such embodiments, the user may be required to ingest the second pill or other substance each time the user takes his medicine. When the indicator reacts with the substance being tested for, a color change of the test area of the reagent test strip may occur. In such an embodiment, the user may be required to place a test strip into his mouth after taking the medicine and store the used test strips in an appropriate container. If and when the user obtains a game result that corresponds to a prize of at least a predetermined value, the user may be required to provide the used test strips as further proof of having taken the medicine. In one embodiment, a reagent test strip may be in the shape of a toothpick.

In one or more embodiments the substance being tested for may include a component that degrades or decomposes over time at a predetermined rate, such that a laboratory may be able to determine a length of time since a particular reagent test strip has been used. For example, a laboratory may be able to determine whether the user used the reagent test strips over time as he was supposed to or used all the reagent strips at once right before sending them into the laboratory.

In yet another embodiment of how a user may be required to further validate compliance, the user may be required to visit a physician or laboratory for testing to verify that the user has been taking the medication. For example, a physician or laboratory may collect a blood sample from the user, for analysis to determine whether the correct dosage of medicine is in the user's bloodstream.

In yet another embodiment of how a user may be required to further validate compliance, the user may be provided with pills that each include a bar code imprinted thereon. The user may also be provided with a bar code scanner. In such an embodiment, the user may be required to scan the bar code of each pill before ingesting the pill. If the user wins a prize (or a prize of at least a predetermined value), the user may be required to provide the data from the bar code scanner to further verify compliance (e.g., by taking the bar code scanner or memory card of the bar code scanner to a pharmacy).

In one or more embodiments, friends or relatives of a user may be allowed to fund one or more prizes for the user. For example, as a birthday present, a granddaughter may provide one-hundred dollars to the system to fund prizes for her grandmother. The granddaughter may even be able to specify how the one-hundred dollars is to be provided to her grandmother. For example, the granddaughter may specify that the one-hundred dollars is to be provided as one large prize or distributed over a plurality of small, frequent prizes. The user may or may not be informed of the source for the funding of the prize. Friends or relative may also be allowed to purchase a chance for the user to win a relatively large prize. For example, a nephew may pay fifty dollars for a chance for his aunt to win one million dollars.

It is understood that some users may miss a dose of medicine occasionally. In one or more embodiments, such occasional misses may be allowed so long as the user admits to the miss after it occurs and before taking the next dose. The documenting module 200 may, for example, track the indication of the miss and the user's acknowledgement of the miss before the taking of the next dose. The documenting module 200 may incorporate this information in the next encrypted code generated for the user.

In one or more embodiments, encoded cap removal data received by the central controller 300 during a compliance verification process may comprise several elements, which may indicate (i) a removal requirement (e.g., the cap should be removed three times per day), (ii) the elapsed time since the last verification (e.g., seven days) and (iii) the number of removals since the last verification (e.g., 21 removals). For example, if an encrypted numeric code is "264180579," upon decryption, the first three digits may indicate a removal requirement, the second three digits may indicate the elapsed time since the last verification, and the final three digits may indicate the number of removals since the last verification. In this manner, the central controller 300 may verify prescription compliance without maintaining and/or continuously updating patient data.

In one or more embodiments, cap removal data may be received by a pharmacy when a user refills a prescription (e.g., the user may provide the cap to the pharmacist at the time of the refill). A benefit may then be provided by the pharmacy (e.g., a 10% discount on prescription medication co-pay). In other embodiments, the pharmacy may transmit cap removal data to a third party (e.g., an insurance company). In one embodiment, the pharmacy that provides a benefit to the user may be reimbursed for at least a portion of the benefit by at least one third party (e.g., the user's insurance company and/or the manufacturer of the medication for which compliance has been verified).

In one or more embodiments, cap removal data may be transmitted to the central controller 300 in a substantially automatic manner (i.e., the transmission of data may require little or no user action). For example, in an embodiment wherein the documenting module 200 comprises a communications port, a program may instruct the module to connect to the central controller 300 (e.g., a modem coupled to the documenting module dials a telephonic number) and transmit cap removal data on a periodic basis (e.g., data is transmitted once per week). In another embodiment, cap removal data is transmitted with each cap removal. In some embodiments, a connection to the central controller 300 may be facilitated via an "always-on" or broadband Internet connection. In this manner, a patient's compliance may be determined and benefits provided in a substantially automatic manner. For example, if the documenting module 200 automatically transmits data to a health insurance agent, all a patient need do is follow a prescription requirement, and the patient may automatically receive a benefit (e.g., a $5 health insurance credit every month).

It should be noted that various rewards or benefits for complying users are envisioned, including but not limited to: (i) priority servicing (e.g., such that patients needn't wait on hold, wait in a line at a pharmacy, etc.), (ii) information on drug trials (pharmaceutical companies may wish to test drugs with to patients who are known to comply with prescriptions, and may pay them for participating), (iii) frequent flyer miles, (iv) prepaid telephone time (e.g., a patient's account is awarded five minutes of phone time for every "success"), and (v) premium entertainment content (e.g., access to pay-per-view television, movies, music, Web sites, etc.).

In one embodiment, a benefit for user compliance may comprise an entry into a sweepstakes. For example, a process for providing a benefit to a user may comprise the following steps: (i) receiving an encrypted code comprising a patient identifier from a patient, (ii) decrypting the code to determine the patient's compliance with a prescription, and if the patient is compliant, (iii) entering the patient identifier in a sweepstakes, (iv) drawing a patient identifier at random, and (v) providing a benefit to the patient associated with the drawn patient identifier. In some embodiments, a patient's identifier may be entered into a sweepstakes more than once. For example, a patient may be entered into a sweepstakes once per each "success." In other embodiments, a patient's number of entries may be based on the length of time the patient is compliant, the patient's "success percentage," etc.

While particular embodiments for carrying out the invention have been described in detail, those familiar with the art to which the invention relates will recognize various alternative designs and embodiments for practicing the invention. These alternative embodiments are within the scope of the present invention.

For example, in one or more embodiments, the documenting module 200 may be included in a pill bottle stand. In one such embodiment, the documenting module 200 may comprise a weight and/or motion sensor, such that the module may be operable to (i) determine a first bottle weight, (ii) detect the removal of the bottle from the stand, (iii) detect the replacement of the bottle on the stand, (iv) determine a second bottle weight, and (v) determine a difference between the first and second bottle weight. In this manner, the documenting module 200 may measure compliance by the removal of the bottle from the stand and its corresponding weight. Such a compliance test may ensure that pills are removed from a bottle (e.g., a "success" may be determined if the second weight is smaller than the first weight).

It should be noted that although cap removal has been described herein as the action monitored to verify compliance, other actions may be monitored within the scope of the present invention. For example, a medicine container may include an accelerometer operable to detect when the medicine container has been lifted or shaken.

In another example, multiple medicine compliance may be encouraged by having the documenting module 200 be associated with a container for multiple medicines (e.g., a holder of multiple medicine containers). In such multiple medicine embodiments, the gaming interface embodiments may also be utilized. For example, if a holder holds six medicine containers, a pharmacist may program a processor of the holder to allow the user six "spins" of the slot machine interface (e.g., every predetermined period of time).

In an alternate embodiment of the present invention, an entity may utilize the functionality of the medicine container described herein to advertise products to the user. For example, a pharmaceutical company may pay to have advertisements for medicines output via an output device of the medicine container. The user may be provided with a game result at the end of such an advertisement, as a reward for viewing the advertisement.

It should be noted that although the embodiments of the present invention have been described with respect to a medicine container, many of the embodiments may be useful for various other types of containers as well. The gaming interface embodiments described above, in particular, may be used for any type of container the opening of which it is desirous to encourage. For example, a soft drink container cap may include a display device for outputting a game result. The game result may be displayed when the soft drink container is first opened or each time the soft drink container is opened or re-closed.

We claim:

1. A method, comprising:
   receiving, from a patient via an authentication device, a code comprising encrypted data descriptive of one or more cap removals of a medicine container;
   decrypting the code via the authentication device; and
   providing a benefit to the patient if the decrypted code indicates that the patient is eligible for the benefit.

2. The method of claim 1, further comprising:
   determining a cap removal requirement associated with the patient;
   determining, based on the decrypted code, that the patient is compliant with the cap removal requirement; and
   determining, based on the patient's compliance with the cap removal requirement, that the patient is eligible to receive the benefit.

3. The method of claim 1, wherein the receiving, decrypting, and providing are conducted by a central controller.

4. The method of claim 3, wherein the central controller comprises an Interactive Voice Response Unit (IVRU).

5. The method of claim 1, wherein the code is received from a telephone associated with the patient.

6. The method of claim 5, wherein the code is received via a Dual-Tone Multi-Frequency (DTMF) transmission from the telephone associated with the patient.

7. The method of claim 1, wherein the code is received by input provided by the patient via a Web interface.

8. The method of claim 1, wherein the code comprises a code output by a container associated with the patient, and wherein the code is further descriptive of a result of a game.

9. The method of claim 8, wherein the game comprises a game of chance.

10. The method of claim 8, wherein the game comprises a game of skill.

11. The method of claim 10, wherein the game comprises a trivia game requiring the patient to answer a plurality of questions.

12. The method of claim 1, wherein the benefit is determined based at least in part on a magnitude of patient compliance associated with the cap removals of the medicine container.

13. The method of claim 1, further comprising:
    requesting, from the patient, a verification of a compliance of the patient with one or more medical instructions.

14. The method of claim 13, further comprising:
    receiving, from the patient, an indication of a verification of compliance of the patient with the one or more medical instructions.

15. The method of claim 14, wherein the benefit is provided at least in part based on the receiving of the indication of the verification of compliance of the patient with the one or more medical instructions.

16. The method of claim 14, wherein the verification of compliance of the patient with the one or more medical instructions is provided via one or more reagent test strips.

17. The method of claim 15, wherein the verification of compliance of the patient with the one or more medical instructions is provided via one or more medical tests.

18. The method of claim 1, wherein the benefit comprises entering the patient into a sweepstakes drawing if the decrypted code indicates that the patient is eligible to be entered into the sweepstakes drawing.

19. The method of claim 18, wherein a probability of the patient winning the sweepstakes is based at least in part on a magnitude of patient compliance associated the cap removals of the medicine container.

20. The method of claim 1, wherein the benefit is funded at least in part by one or more of a friend and a relative of the patient.

21. The method of claim 20, wherein the benefit is defined by the one or more of the friend or relative.

22. The method of claim 1, wherein a value of the benefit is based at least in part on a number of successes associated with the one or more cap removals of the medicine container.

23. The method of claim 1, wherein the data descriptive of the one or more cap removals of the medicine container is determined by a pill bottle stand.

24. The method of claim 23, wherein the data descriptive of the one or more cap removals of the medicine container is determined by the pill bottle stand by utilizing a weight sensor.

25. The method of claim 23, wherein the data descriptive of the one or more cap removals of the medicine container is determined by the pill bottle stand by utilizing a motion sensor.

26. The method of claim 1, wherein the code is generated by the medicine container in response to the one or more cap removals of the medicine container.

27. A container, comprising:
a processor; and
a storage device in communication with said processor and storing instructions adapted to be executed by said processor to:
receive, from a patient, a code comprising encrypted data descriptive of one or more cap removals of the container;
decrypt the code; and
provide a benefit to the patient if the decrypted code indicates that the patient is eligible for the benefit.

28. A medium storing instructions adapted to be executed by a processor to:
receive, from a patient, a code comprising encrypted data descriptive of one or more cap removals of a medicine container;
decrypt the code; and
provide a benefit to the patient if the decrypted code indicates that the patient is eligible for the benefit.

* * * * *